(12) United States Patent
Horiba et al.

(10) Patent No.: US 8,102,113 B2
(45) Date of Patent: Jan. 24, 2012

(54) QUINOXALINE-CONTAINING COMPOUNDS AND POLYMERS THEREOF

(75) Inventors: Koji Horiba, Kanagawa (JP); Hidekazu Hirose, Kanagawa (JP); Takeshi Agata, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 703 days.

(21) Appl. No.: 12/041,277

(22) Filed: Mar. 3, 2008

(65) Prior Publication Data

US 2008/0306239 A1 Dec. 11, 2008

(30) Foreign Application Priority Data

Jun. 7, 2007 (JP) ................. 2007-151370

(51) Int. Cl.
| | |
|---|---|
| H01L 51/54 | (2006.01) |
| H05B 33/14 | (2006.01) |
| C09K 11/06 | (2006.01) |
| C08G 63/66 | (2006.01) |
| C07D 241/36 | (2006.01) |

(52) U.S. Cl. ... 313/504; 313/506; 257/40; 257/E51.051; 428/690; 428/917; 528/301; 544/353

(58) Field of Classification Search .......... None
See application file for complete search history.

(56) References Cited

U.S. PATENT DOCUMENTS

| | | | | |
|---|---|---|---|---|
| 4,092,162 | A | | 5/1978 | Wright et al. |
| 4,539,507 | A | | 9/1985 | VanSlyke et al. |
| 4,769,292 | A | * | 9/1988 | Tang et al. ............... 428/690 |
| 4,801,517 | A | | 1/1989 | Frechet et al. |
| 4,806,443 | A | | 2/1989 | Yanus et al. |
| 4,806,444 | A | | 2/1989 | Yanus et al. |
| 4,937,165 | A | | 6/1990 | Ong et al. |
| 4,959,288 | A | | 9/1990 | Ong et al. |
| 4,983,482 | A | | 1/1991 | Ong et al. |
| 5,034,296 | A | | 7/1991 | Ong et al. |
| 5,674,635 | A | * | 10/1997 | Hsieh et al. ............... 428/690 |
| 5,879,821 | A | * | 3/1999 | Hsieh ....................... 428/690 |
| 6,652,995 | B2 | * | 11/2003 | Seki et al. ................. 428/690 |
| 6,670,052 | B2 | * | 12/2003 | Hirose et al. .............. 428/690 |
| 7,166,859 | B2 | * | 1/2007 | Hirose et al. .............. 257/40 |
| 2001/0024738 | A1 | * | 9/2001 | Hawker et al. ............ 428/690 |
| 2003/0207187 | A1 | | 11/2003 | Seki et al. |
| 2004/0018384 | A1 | * | 1/2004 | Hirose et al. .............. 428/690 |
| 2004/0081854 | A1 | * | 4/2004 | Hirose et al. .............. 428/690 |
| 2005/0014020 | A1 | * | 1/2005 | Yoneyama et al. ........ 428/690 |
| 2005/0065342 | A1 | | 3/2005 | Shitagaki et al. |
| 2005/0186446 | A1 | * | 8/2005 | Shitagaki et al. .......... 428/690 |
| 2006/0046094 | A1 | * | 3/2006 | Nishino et al. ............. 428/690 |
| 2006/0267487 | A1 | * | 11/2006 | Ozaki et al. ............... 313/504 |
| 2007/0059553 | A1 | | 3/2007 | Egawa et al. |
| 2007/0148493 | A1 | * | 6/2007 | Yoneyama et al. ........ 428/690 |
| 2007/0281076 | A1 | * | 12/2007 | Okuda et al. .............. 427/66 |
| 2008/0306239 | A1 | | 12/2008 | Horiba et al. |
| 2008/0311425 | A1 | * | 12/2008 | Okuda et al. .............. 428/690 |
| 2009/0001876 | A1 | * | 1/2009 | Okuda et al. .............. 313/504 |

FOREIGN PATENT DOCUMENTS

| | | |
|---|---|---|
| CN | 1445258 A | 10/2003 |
| JP | 53-53676 | 5/1978 |
| JP | B2-59-028903 | 7/1984 |
| JP | A-59-194393 | 11/1984 |
| JP | A-61-020953 | 1/1986 |
| JP | A-01-134456 | 5/1989 |
| JP | A-01-134457 | 5/1989 |
| JP | A-01-134462 | 5/1989 |
| JP | A-04-133065 | 5/1992 |
| JP | A-04-133066 | 5/1992 |
| JP | A-5-148350 | 6/1993 |
| JP | A-10-92576 | 4/1998 |
| JP | A-2006-16384 | 1/2006 |
| JP | A-2008-303169 | 12/2008 |

OTHER PUBLICATIONS

Thomas et al., Journal of the American Chemical Society, (2001), vol. 123, pp. 9404-9411.*
Thomas et al., Chemistry of Materials, (2002), vol. 14, pp. 2796-2802.*
Sugihara et al., "Synthesis and Physical Properties of Polyphosphazenes Having Hole-Transporting Aromatics Tertiary Amines in Side Chains," *Polymer Preprints*, Japan, 1993, vol. 42, No. 7 20J-21, p. 2860-2863.

(Continued)

*Primary Examiner* — Jennifer Chriss
*Assistant Examiner* — Brett A Crouse
(74) *Attorney, Agent, or Firm* — Oliff & Berridge, PLC

(57) ABSTRACT

There is provided a quinoxaline-containing compound represented by the following formula (I);

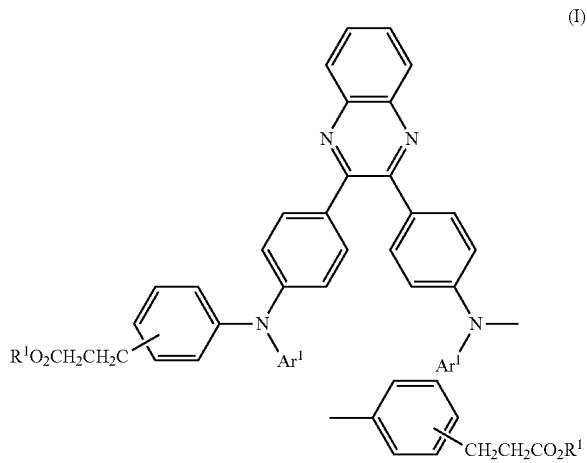

wherein $Ar^1$ represents a substituted or unsubstituted monovalent aromatic group; and $R^1$ represents a hydrogen atom, a substituted or unsubstituted alkyl group, a substituted or unsubstituted aryl group, or a substituted or unsubstituted aralkyl group.

7 Claims, 6 Drawing Sheets

OTHER PUBLICATIONS

Gustafsson et al., "Flexible light-emitting diodes made from soluble conducting polymers," *Nature*, 1992, vol. 357, p. 477-479.
Mori et al., "Light-Emitting Characteristics of Organic Electroluminescent Devices with a Mixed-Layer Structure," *The 38th Spring Meeting of The Japan Society of Applied Physics and Related Societies*, 1991, 31p-G-12, p. 1086.
Oct. 11, 2010 Chinese Office Action issued in Chinese Patent Application No. 200810082691.9 (with translation).
Nov. 9, 2010 Office Action issued in U.S. Appl. No. 12/051,479.
Apr. 14, 2011 Office Action issued in U.S. Appl. No. 12/051,479.
Sep. 13, 2011 Office Action issued in U.S. Appl. No. 12/051,479.
U.S. Appl. No. 12/051,479, filed Mar. 19, 2008, to Horiba et al.
Thin Solid Films, 94, 1982, pp. 171-183.
Appl. Phys. Lett. vol. 51, Sep. 21, 1987, pp. 913-915.
Technical Report of IEICE, OME95-54, 1995, pp. 47-52.
Proceedings of the $40^{th}$ Applied Physics Related Associated Seminar, 30a-SZK-14, 1993.
Proceedings of the $38^{th}$ Applied Physics Related Associated Seminar, 31p-G-12, 1991.
Proceedings of the $50^{th}$ Applied Physics Society Seminar, 29p-ZP-5, 1989.
Proceedings of the 51th Applied Physics Society Seminar, 28a-PB-7, 1990.

\* cited by examiner

QUINOXALINE-CONTAINING COMPOUNDS AND POLYMERS THEREOF

CROSS-REFERENCE TO RELATED APPLICATIONS

This application is based on and claims priority under 35 USC 119 from Japanese Patent Application No. 2007-151370 filed on Jun. 7, 2007.

BACKGROUND

1. Technical Field

The present invention relates to a novel quinoxaline-containing compound and polymers of the quinoxaline-containing compound.

2. Related Art

As a charge transporting material, charge transporting polymers represented by polyvinyl carbazole (PVK), and those of a low-molecular dispersion system wherein a charge-transporting low-molecular compound is dispersed in a polymer are well known. Among the aforementioned materials, materials of the low-molecular dispersion system are principally used particularly for electrophotographic photoreceptors in view of multiplicity of materials and the possibility of high-performance due to the combination of a low-molecular compound and a polymer and the like.

SUMMARY

According to an aspect of the present invention, there is provided a quinoxaline compound represented by the following formula (I):

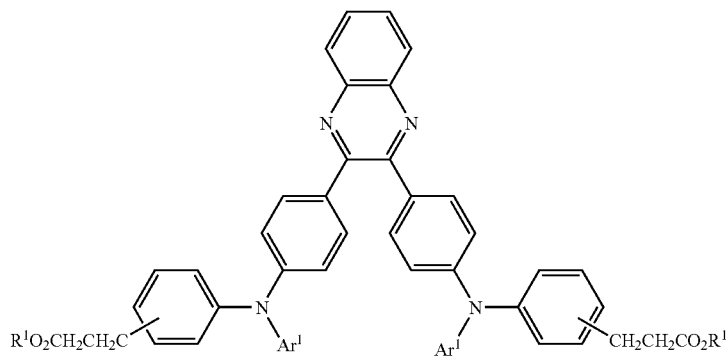

wherein $Ar^1$ represents a substituted or unsubstituted monovalent aromatic group, and $R^1$ represents a hydrogen atom, a substituted or unsubstituted alkyl group, a substituted or unsubstituted aryl group, or a substituted or unsubstituted aralkyl group.

BRIEF DESCRIPTION OF THE DRAWINGS

Exemplary embodiments of the present invention will be described in detail based on the following figures, wherein.

DETAILED DESCRIPTION

Figure 1:
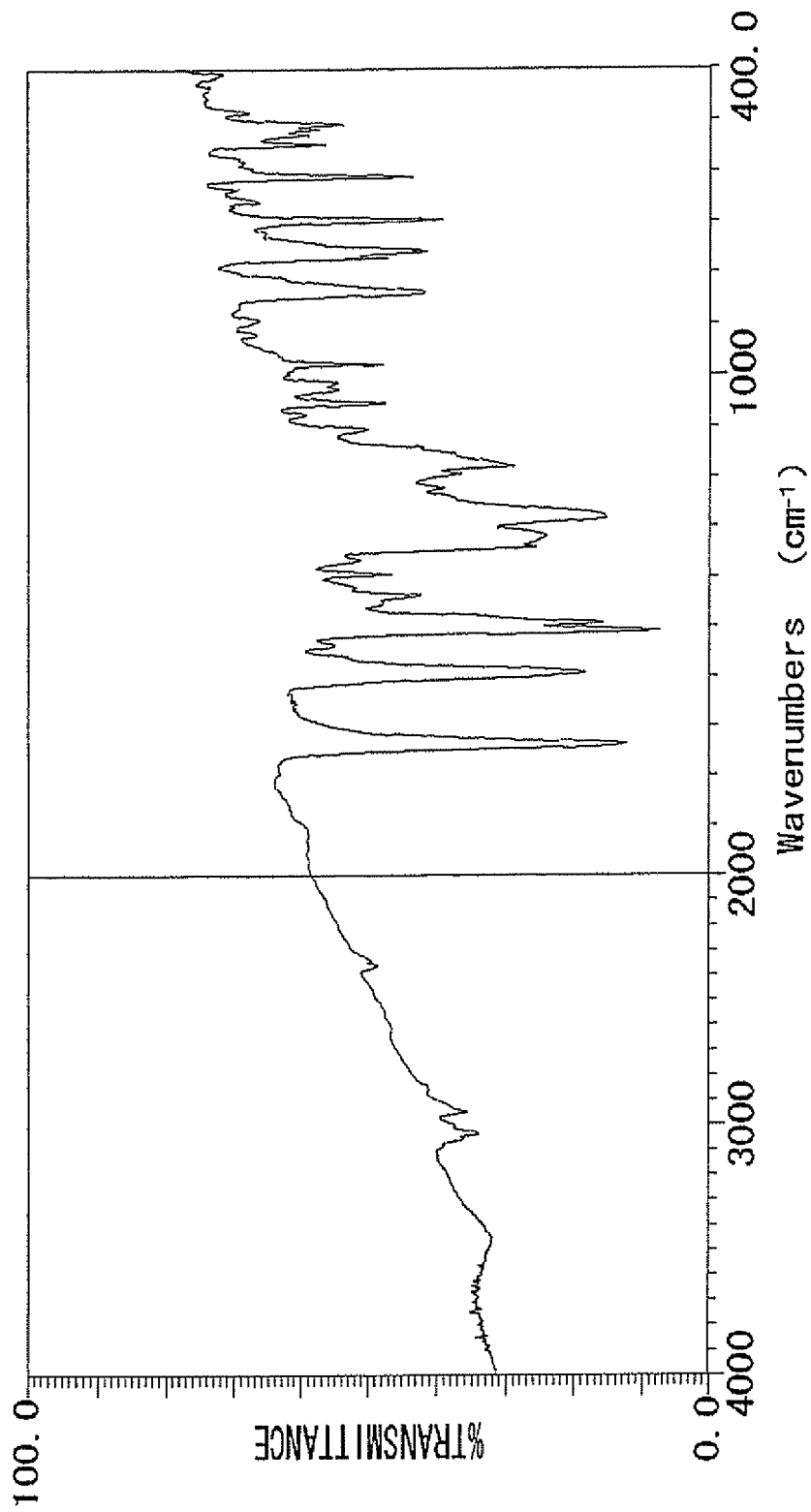
FIG. 1 is the IR spectrum of the compound obtained by example 1.

The quinoxaline-containing compound of an exemplary embodiment is represented by the following formula (I):

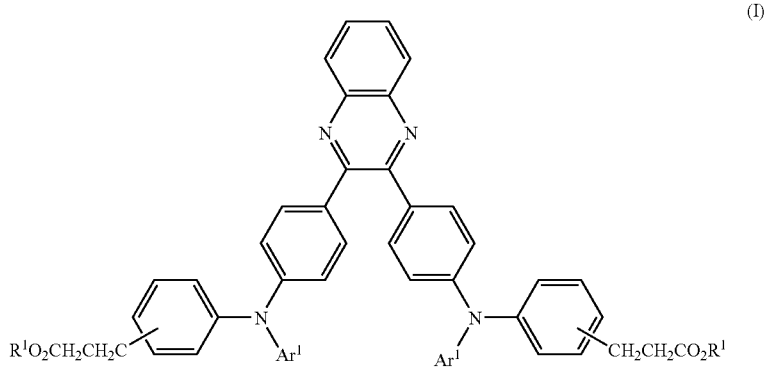

wherein $Ar^1$ represents a substituted or unsubstituted monovalent aromatic group, and $R^1$ represents a hydrogen atom, a substituted or unsubstituted alkyl group, a substituted or unsubstituted aryl group, or a substituted or unsubstituted aralkyl group.

In the above-described formula (I), $Ar^1$ represents a substituted or unsubstituted monovalent aromatic group wherein although the number of aromatic ring or heterocyclic ring is not specifically limited, preferred examples thereof include as substituted or unsubstituted phenyl groups specifically a substituted or unsubstituted monovalent polynuclear aromatic hydrocarbon having from 2 to 20 aromatic ring number, a substituted or unsubstituted monovalent condensed aromatic hydrocarbon having from 2 to 20 aromatic ring number, a substituted or unsubstituted monovalent aromatic heterocyclic ring, or a substituted or unsubstituted monovalent aromatic group containing at least one aromatic heterocyclic ring.

The polynuclear aromatic hydrocarbon means specifically polycyclic aromatic hydrocarbon defined below in the invention. Namely, the "polynuclear aromatic hydrocarbon" represents a hydrocarbon wherein two or more aromatic rings constituted from carbon and hydrogen exist, and the rings are bonded to each other through a carbon-carbon bond. A specific example includes biphenyl, terphenyl, and stilbene.

The condensed aromatic hydrocarbon means specifically the polynuclear aromatic hydrocarbon defined below in the invention. Namely, the "condensed aromatic hydrocarbon" represents a hydrocarbon wherein 2 or more of aromatic rings constituted from carbon and hydrogen exist, and these aromatic rings share with a pair of adjacent bonded hydrocarbons, respectively. Specific examples thereof include naphthalene, anthracene, phenanthrene, pyrene, perylene, and fluorene.

In the formula (I), the aromatic heterocyclic ring selected as one of the structures indicating $Ar^1$ represents an aromatic ring containing also the elements other than carbon and hydrogen. The number of atoms (Nr) constituting the ring skeleton of Nr=5 and/or 6 is preferably applied.

Although the type and the number of atoms (heteroatoms) other than the carbon atoms constituting the ring skeleton are not limited, for example, sulfur atoms, nitrogen atoms, oxygen atoms and the like are preferably used wherein two or more types of and/or two or more of heteroatoms may be contained in the ring skeleton. Particularly, as a heterocyclic ring having a five-membered heterocyclic ring structure, thiophene, pyrrole, furan, or the heterocyclic rings of them wherein the carbons at 3- and 4-positions are further substituted by nitrogen are preferably used; and pyridine ring is preferably used as a heterocyclic ring having a six-membered ring structure.

The aromatic group containing the aromatic heterocyclic ring selected as one of the structures representing $Ar^1$ in the formula (I) designates a linking group containing at least one of the above-described aromatic heterocyclic rings in the atomic group forming a skeleton. They may be either the ones the whole part thereof is constituted from a conjugated system, or the ones a part thereof is constituted from a conjugated system. However, the ones the whole part thereof is constituted from a conjugated system are preferable in view of charge transportability or luminous efficiency.

Examples of the substituent which may be introduced into the monovalent aromatic group represented by $Ar^1$ in the formula (I) include, for example, hydrogen atom, alkyl group, alkoxy group, phenoxy group, aryl group, aralkyl group, substituted amino group, halogen atom and the like.

An alkyl group as the substituent to be introduced to the above-described monovalent aromatic group has preferably from 1 to 10 carbon atoms, and the alkyl group having from 1 to 6 carbon atoms is more preferable. A specific example includes methyl group, ethyl group, propyl group, isopropyl group and the like.

An alkoxy group as the substituent to be introduced to the above-described monovalent aromatic group has preferably from 1 to 10 carbon atoms, and the alkoxy group having from 1 to 6 carbon atoms is more preferable. A specific example includes methoxy group, ethoxy group, propoxy group, isopropoxy group and the like.

An aryl group as the substituent to be introduced to the above-described monovalent aromatic group has preferably from 6 to 20 carbon atoms, and the aryl group having from 6 to 12 carbon atoms is more preferable. Specific examples include phenyl group, toluoyl group and the like.

An aralkyl group as the substituent to be introduced to the above-described monovalent aromatic group has preferably from 7 to 20 carbon atoms, and the aralkyl group having from 7 to 15 carbon atoms is more preferable. A specific example includes benzyl group, phenetyl group and the like.

Examples of the substituent in the substituted amino group as the substituent to be introduced to the above-described monovalent aromatic group include an alkyl group, an aryl group, and an aralkyl group wherein specific examples and preferred ranges of the characteristics of them may be the same as the above-mentioned alkyl groups, aryl groups, and aralkyl groups.

Specific examples and preferred ranges of the characteristics of the alkyl group, the aryl group, and the aralkyl group represented by $R^1$ in the formula (I) may be the same as the above-mentioned alkyl groups, aryl groups, and aralkyl groups. Furthermore, $R^1$ in the formula (I) is more preferably a straight-chain or branched alkyl group having from 1 to 10 carbon atoms.

Meanwhile, an example of the substituent which may be introduced to the alkyl croup, the aryl group and the aralkyl group represented by $R^1$ includes alkyl group, alkoxy group, phenoxy group, aryl group, aralkyl group, substituted amino croup, halogen atom and the like.

Specific examples and preferred ranges of the characteristics of these introducible substituents may be the same as that of the substituents enumerated as the ones which may be introduced to the $Ar^1$ in the formula (I).

In the formula (I), a more preferable combination is in that $Ar^1$ is a phenyl group, and $R^1$ is a methyl group.

In the formula (I), a still more preferable combination is in that $Ar^1$ is a biphenyl group, and $R^1$ is a methyl group.

Specific examples of the quinoxaline-containing compounds represented by the formula (I) will be shown hereinbelow. Although exemplified examples 1 to 22 are shown, the invention is not limited thereto.

Any of the specific examples enumerated in the following list exhibits symmetrical appearance centering around the median quinoxaline. In the following list, the first left column indicates the number of an exemplified compound, the second column indicates $Ar^1$ in the formula (I), the third column indicates the bonding position of "$R^1O_2CH_2CH_2C—$" in the following formula (I), and the fourth column indicates $R^1$ in the formula (I).

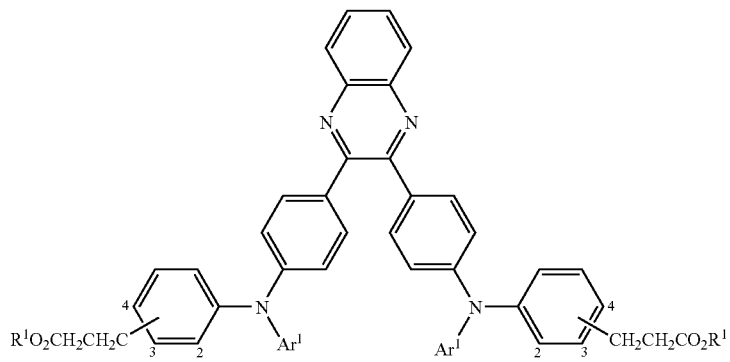

Formula (I)

wherein $Ar^1$ represents a substituted or unsubstituted monovalent aromatic group, and $R^1$ represents a hydrogen atom, substituted or unsubstituted alkyl group, substituted or unsubstituted aryl group, or substituted or unsubstituted aralkyl group.

| Structure | Ar | Bonding Position | $R^1$ |
|---|---|---|---|
| 1 | phenyl | 3 | —H |
| 2 | phenyl | 4 | —CH$_3$ |
| 3 | 4-methylphenyl | 3 | —CH$_3$ |
| 4 | 4-methylphenyl | 4 | —CH$_3$ |
| 5 | 2,3-dimethylphenyl | 4 | phenyl |
| 6 | 4-biphenyl | 4 | —CH$_3$ |
| 7 | 4-terphenyl | 4 | —CH$_2$CH$_2$CH$_2$CH$_2$CH$_2$CH$_3$ |
| 8 | 1-naphthyl | 4 | benzyl |

-continued

| Structure | Ar | Bonding Position | R¹ |
|---|---|---|---|
| 9 | 9-anthracenyl | 4 | —CH₂CH₂CH₂CH₃ |
| 10 | 1-methyl-phenanthrenyl | 4 | —CH₂CH₂CH₂CH₃ |
| 11 | 4-(1H-pyrrol-1-yl)phenyl | 4 | —CH₃ |
| 12 | 1-pyrenyl | 4 | —CH₃ |
| 13 | 4-(2-phenylethenyl)phenyl | 4 | —CH₂CH₃ |
| 14 | 4-(thiophen-2-yl)phenyl | 4 | 4-methylphenyl |
| 15 | 4-(2,2'-bithiophen-5-yl)phenyl | 4 | —CH₃ |
| 16 | 4-[2-(4-n-hexylthiophen-2-yl)ethenyl]phenyl | 4 | —CH₃ |
| 17 | 4'-[2-(thiophen-2-yl)ethenyl]biphenyl-4-yl | 4 | —C(CH₃)₃ |
| 18 | 4-[5-(4-tert-butylphenyl)-1,3,4-oxadiazol-2-yl]phenyl | 4 | —CH₃ |

| Structure | Ar | Bonding Position | R¹ |
|---|---|---|---|
| 19 | 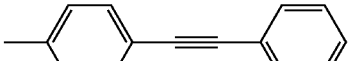 | 4 | —CH₃ |
| 20 | 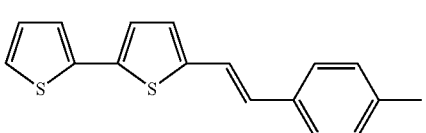 | 4 | —CH₂CH₂CH₂CH₂CH₂CH₂CH₂CH₃ |
| 21 | 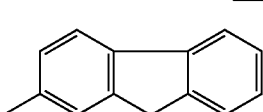 | 4 | —CH₂CH₂CH₃ |
| 22 | 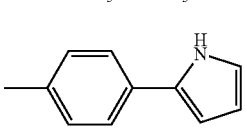 | 4 | 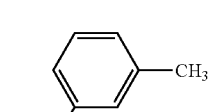 |

The polymers of quinoxaline-containing compound according to an exemplary embodiment are represented by the following formula (II).

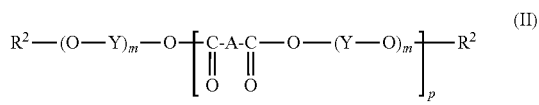

wherein Y represents substituted or unsubstituted divalent hydrocarbon group, $R^2$ represents a hydrogen atom, substituted or unsubstituted alkyl group, substituted or unsubstituted aryl group, or substituted or unsubstituted aralkyl group, m is an integer of from 1 to 5, p is an integer of from 5 to 5,000, and A is a group represented by the following structural formula (III).

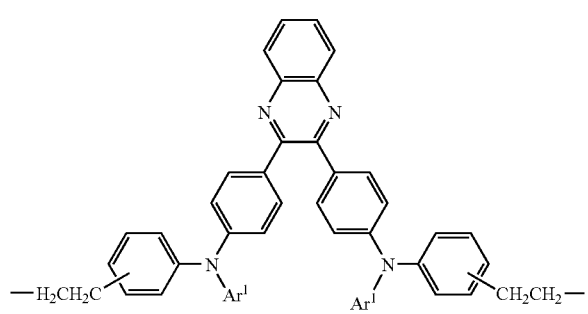

wherein $Ar^1$ represents a substituted or unsubstituted monovalent aromatic group.

The substituted or unsubstituted divalent hydrocarbon group represented by Y in the above-described formula (II) is the group selected from the following structural formulae (IV-1) to (IV-7).

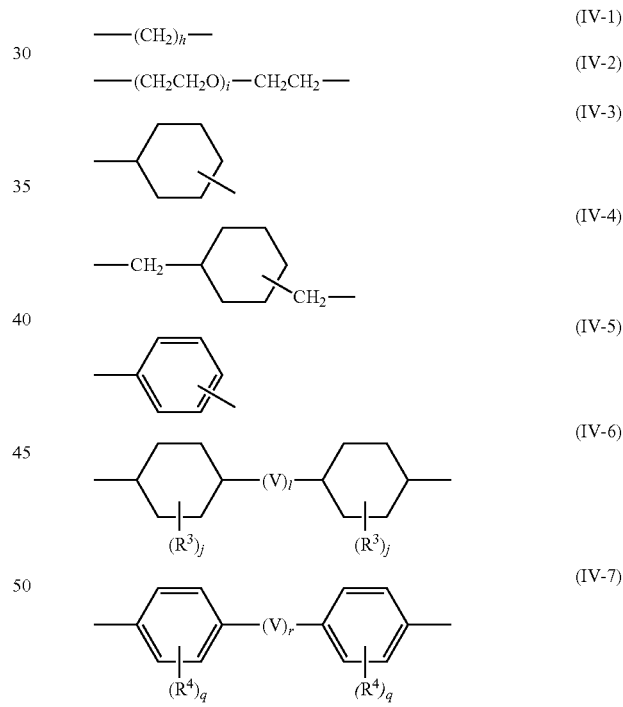

In structural formulae (IV-1) to (IV-7), $R^3$ and W each independently represent a hydrogen atom, a substituted or unsubstituted alkyl group each having from 1 to 4 carbon atoms, a substituted or unsubstituted alkoxy group each having from 1 to 4 carbon atoms, a substituted or unsubstituted phenyl group, or substituted or unsubstituted aralkyl group; h and i each independently represent an integer of from 1 to 10; l and r each independently represent 0 or 1; j and q each independently represent an integer of from 0 to 2; and V represents a group selected from the following structural formulae (V-1) to (V-11).

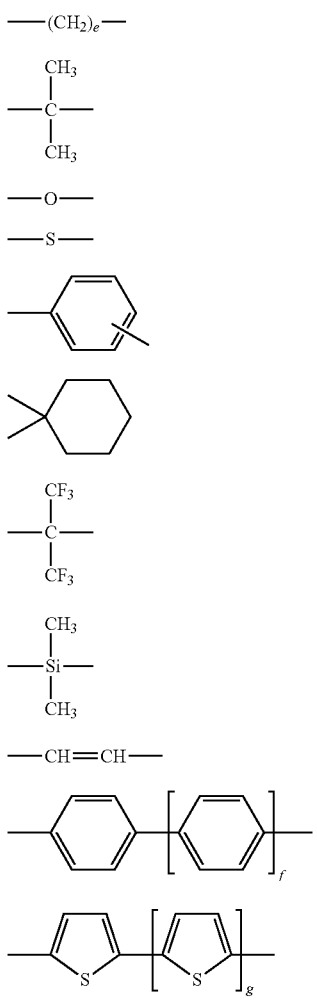

(V-1)
(V-2)
(V-3)
(V-4)
(V-5)
(V-6)
(V-7)
(V-8)
(V-9)
(V-10)
(V-11)

In structural formulae (V-1), (V-10) and (V-11), e is an integer of from 1 to 5, and f and g each independently represent an integer of from 0 to 5.

Although it is preferred that a polymerization degree p of the polymer of the quinoxaline-containing compound represented by the formula (II) is from 5 to 5,000, more preferable is in a range of from 10 to 1,000 in view of film forming property, the stability of an element and the like. Meanwhile, it is preferred that a weight average molecular weight Mw of the polymer is in a range of from 10,000 to 300,000, and more preferably is in a range of from 10,000 to 150,000.

The alkyl group, the aryl group or the aralkyl group represented by $R^2$ in the formula (II) are the same as the alkyl group, the aryl group or the aralkyl group represented by $R^1$ in the formula (I), and the preferable range thereof is also the same as that of the latter. The substituents which may be introduced to the respective substituents represented by $R^2$ in the formula (II) are the same as those enumerated as the substituents which may be introduced to the alkyl group, the aryl group, and the aralkyl group represented by $R^1$ in the formula (I), and the preferable range thereof is also the same as that of the latter.

Among others, hydrogen atom, and unsubstituted aryl groups are more preferable in view of a synthetic problem being in easily substitutable.

A more preferable combination in the formula (II) is in that Y is an ethylene glycol, $Ar^1$ is a biphenyl, $R^2$ is a hydrogen, m is an integer of from 1 to 3, and p is an integer of from 10 to 500.

Still further preferable are in that m is 1, and p is an integer of from 10 to 200.

The $Ar^1$ in the structural formula (III) is the same as that of the $Ar^1$ in the formula (I).

Specific examples of the polymers of the quinoxaline-containing compounds represented by the formula (II) will be shown hereinbelow as exemplified examples (1) to (27). However, it should be noted that the invention is not limited to these specific examples. In the following list, the left most column indicates the number of an exemplified compound, the second column from the left indicates A in the formula (II) wherein the number specified corresponds to that of the exemplified examples in the above-described list; and "$CO_2R^1$" at the both ends of the compound concerned are removed and the groups to be applied as bonding hands are entered to that positions. The third column from the left indicates a molar ratio representing the ratio of the respective groups in the case where the groups to be entered to the A are plural. The fourth column from the left indicates the Y in the formula (II). The fifth column from the left indicates the m in the formula (II), the sixth column from the left indicates the p in the formula (II), and the seventh column indicates the $R^2$ in the formula (II).

| Polymer | A Structure in Table 1 (No.) | Ratio | Y | m | P | $R^2$ |
|---|---|---|---|---|---|---|
| (1) | 2 | — | —(CH$_2$)$_2$— | 1 | 76 | —CH$_3$ |
| (2) | 2 | — | (cyclohexylene) | 1 | 80 | —CH$_3$ |
| (3) | 2 | — | (phenyl-CH$_2$-phenyl) | 1 | 82 | —CH$_3$ |
| (4) | 4 | — | —(CH$_2$)$_2$— | 1 | 75 | —CH$_3$ |

-continued

| Polymer | A Structure in Table 1 (No.) | Ratio | Y | m | P | R² |
|---|---|---|---|---|---|---|
| (5) | 4 | — | [1,4-diethylcyclohexane] | 1 | 96 | —CH₃ |
| (6) | 4 | — | [dicyclohexylmethane] | 1 | 92 | —CH₃ |
| (7) | 6 | — | —(CH₂)₂— | 1 | 79 | —CH₃ |
| (8) | 6 | — | [1,3-phenylene] | 1 | 56 | —CH₃ |
| (9) | 6 | — | —(CH₂)₆— | 1 | 67 | —CH₃ |
| (10) | 8 | — | —(CH₂)₂— | 1 | 71 | [benzyl] |
| (11) | 8 | — | —(CH₂)₆— | 1 | 70 | [benzyl] |
| (12) | 11 | — | —(CH₂)₂— | 1 | 65 | —CH₃ |
| (13) | 11 | — | —(CH₂)₆— | 1 | 69 | —CH₃ |
| (14) | 11 | — | [1,4-cyclohexylene] | 1 | 72 | —CH₃ |
| (15) | 11 | — | [1,4-diethylcyclohexane] | 1 | 76 | —CH₃ |
| (16) | 14 | — | —(CH₂)₂— | 1 | 74 | [4-methylphenyl] |
| (17) | 14 | — | [1,3-bis(methylene)benzene] | 1 | 48 | [4-methylphenyl] |
| (18) | 14 | — | [dicyclohexylmethane] | 1 | 59 | [4-methylphenyl] |
| (19) | 18 | — | —(CH₂)₂— | 1 | 73 | —CH₃ |
| (20) | 18 | — | [diphenylmethane] | 1 | 42 | —CH₃ |
| (21) | 18 | — | —(CH₂)₆— | 1 | 67 | —CH₃ |
| (22) | 21 | — | —(CH₂)₂— | 1 | 70 | —CH₂CH₂CH₃ |
| (23) | 21 | — | —(CH₂)₆— | 1 | 73 | —CH₂CH₂CH₃ |

| Polymer | A Structure in Table 1 (No.) | Ratio | Y | m | P | $R^2$ |
|---|---|---|---|---|---|---|
| (24) | 21 | — | —CH$_2$—⬡—CH$_2$— | 1 | 46 | —CH$_2$CH$_2$CH$_3$ |
| (25) | 2/6 | 1/1 | —(CH$_2$)$_2$— | 1 | 54 | —CH$_3$ |
| (26) | 2/11 | 1/1 | —(CH$_2$)$_2$— | 1 | 85 | —CH$_3$ |
| (27) | 6/11 | 1/1 | —(CH$_2$)$_2$— | 1 | 76 | —CH$_3$ |

The quinoxaline-containing compounds in the above-mentioned exemplary embodiment may be synthesized, for example, as described hereunder.

(1) They may be synthesized by reacting an arylamine with a carboalkoxyalkylbenzene halide, or reacting an aryl halide with a carboalkoxyaniline to synthesize diarylamine, and then, reacting the resulting diarylamine with a bishalogenated aryl.

(2) They may be synthesized by reacting an arylamine or a benzidine derivative with a carboalkoxyalkylbenzene halide to synthesize a diarylamine, and then, reacting the resulting diarylamine with aryl halide.

As to a synthesis of a charge transporting material having an alkylenecarboxylic ester group, a method wherein a chloromethyl group is introduced into the material, thereafter Grignard reagent is formed with Mg, the resulting product is converted with carbon dioxide to carboxylic acid, and then, the product is esterified is described in JP-A No. 5-80550. In this method, however, since the chloromethyl group exhibits high reactivity, it may not be introduced in the initial stage of the raw material. Accordingly, there are necessary such procedures that a skeleton of triarylamine, tetraarylbenzidine or the like is formed, and then, for example, the methyl group which has been introduced in the initial stage of the raw material is chloromethylated; or that an unsubstituted material is used in the raw material stage, a tetraarylbenzidine skeleton is formed, then, a functional group such as formyl group is introduced in accordance with the substitution reaction to an aromatic ring, thereafter the reaction product is reduced to obtain an alcohol, and further, a halogenating reagent such as thionyl chloride is used to be introduced to a chloromethyl croup, or it is directly chloromethylated by paraformaldehyde and hydrochloric acid or the like.

However, since a charge transporting material having a skeleton such as triarylamine or tetraarylbenzidine exhibits very high reactivity, halogen substitution reaction into an aromatic ring arises easily in accordance with the method wherein the methyl group which has been introduced is chloromethylated. Accordingly, only the methyl group may not substantially be chlororated selectively. Moreover, in such a method that an unsubstituted material is used in the raw material stage, a functional group such as formyl group is introduced, and then, it is introduced to chloromethyl group; and a method for chloromethylating directly a material, the chloromethyl group may be introduced into only para position with respect to nitrogen atom, so that alkylenecarboxylic ester croup may be introduced to only the para position with respect to nitrogen atom.

On the other hand, a method wherein a formyl group is introduced to a material, and then, it is introduced to chloromethyl group accompanies a long reaction step, while a method for obtaining a monomer by reacting arylamine or diarylbenzidine with carboalkoxyalkylbenzene halide is excellent in that the position of a substituent may be changed to easily control ionization potential or the like, so that it becomes possible to control a compound. With respect to the monomer used in the synthesis in the exemplary embodiment, a variety of substituents may be easily introduced at an arbitrary position of a compound; and the monomer is chemically stable, so that the handling thereof is easy. Thus, the above-mentioned problems are improved.

A method for manufacturing a quinoxaline-containing compound according to an exemplary embodiment will be described specifically. In the exemplary embodiment, coupling reaction is subjected to, for example, the halogen compound represented by the following formula (VI) and the acetamide compound represented by the following formula (VII) with a copper catalyst, or coupling reaction is subjected to the acetamide compound represented by the following formula (VIII) and the halogen compound represented by the following formula (IX) with a copper catalyst to obtain the diarylamine represented by the following formula (X), and then, coupling reaction is subjected to the diarylamine (X) and the dihalogen compound represented by the following formula (XI) with a copper catalyst, whereby the quinoxaline compound may be obtained.

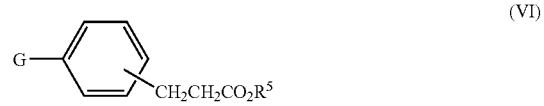

(VI)

wherein $R^5$ represents a hydrogen atom, a substituted or unsubstituted alkyl group, a substituted or unsubstituted aryl group, or a substituted or unsubstituted aralkyl group; and G represents a chlorine atom, a bromine atom, or an iodine atom.

$Ar^1$—NHAc (VII)

wherein $Ar^1$ is the Same as the $Ar^1$ in the Formula (I) or (III), and Ac is an Acetyl group.

(VIII)

wherein R⁵ represents a hydrogen atom, a substituted or unsubstituted alkyl group, a substituted or unsubstituted aryl group, or a substituted or unsubstituted aralkyl group; and Ac represents an acetyl group.

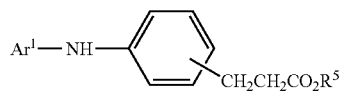

wherein Ar¹ is the same as the Ar¹ in the formula (I) or (III), and G is the same as the G in the formula (VI)

$$Ar^1—NH—\underset{CH_2CH_2CO_2R^5}{\bigcirc}$$ (X)

wherein Ar¹ is the same as the Ar¹ in the formula (I) or (III), and R⁵ is the same as the R⁵ in the formula (VI) or (VIII).

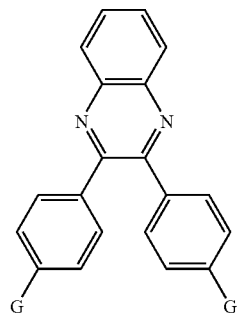

wherein G is the same as the G in the formula (VI) or (IX).

In the coupling reaction, from 1.0 to 1.5 equivalents, and more preferably from 1.0 to 1.2 equivalents halogen compound represented by the formula (VI) or (IX) is used with respect to 1 equivalent of the acetamide compound represented by the formula (VII) or (VIII).

A copper powder, copper oxide, copper sulfate or the like is used as the copper catalyst; and preferably from 0.001 to 3 parts by mass, and more preferably from 0.01 to 2 parts by mass of the copper catalyst are used with respect to 1 part by mass of the acetamide compound represented by the formula (VII) or (VIII).

Potassium phosphate, sodium carbonate, potassium carbonate or the like may be used as the base to be applied to the coupling reaction; and preferably from 0.5 to 3 equivalent, and more preferably from 0.7 to 2 equivalent of the base are used with respect to 1 equivalent of the acetamide compound represented by the formula (VII) or (VIII).

Although solvent is not necessarily used in the above-described coupling reaction, a preferable example of the solvent, if it is used, includes water-insoluble hydrocarbon system solvent having a high boiling point such as n-tridecane, tetrarine, p-cymen, and terpinolene; or halide system solvent having a high boiling point such as o-dichlorobenzene, and chlorobenzene. In a range of from preferably from 0.1 to 3 parts by mass of, and more preferably from 0.2 to 2 parts by mass of the solvent may be used with respect to 1 part by mass of the acetamide compound represented by the formula (VII) or (VIII).

It is preferred that the coupling reaction is conducted under the inert gas such as nitrogen, and argon atmosphere in the temperature range of preferably from 100° C. to 300° C., more preferably from 150° C. to 270° C., and still further preferably from 180° C. to 230° C. while the mixture is sufficiently stirred efficiently; and further wile the water produced in the reaction is removed. After the reaction, the reaction product is cooled as occasion demands, and then, the product is hydrolyzed by the use of a solvent such as methanol, ethanol, n-octanol, ethylene glycol, propylene glycol, and glycerin, and a base such as sodium hydrate, and potassium hydrate.

An applied amount of the solvent in this case is from 0.5 to 10 parts by mass, and preferably from 1 to 5 parts by mass with respect to 1 part by mass of the acetamide compound represented by the formula (VII) or (VIII), while the base is used in an amount of preferably from 0.2 to 5 part by mass, and more preferably from 0.3 to 3 parts by mass with respect to 1 part by mass of the acetamide compound represented by the formula (VII) or (VIII).

The hydrolysis reaction is conducted after the coupling reaction by directly adding the solvent and the base to the reaction solution and sufficiently and efficiently agitating the mixture under an inert gas atmosphere such as a nitrogen or argon atmosphere in a temperature range of from 50° C. to the boiling point of the solvent. In this case, since a carboxylate is produced in the coupling reaction and solidified, it is particularly preferred to use a solvent having a high boiling point of 150° C. or more by the use of which the reaction temperature may be elevated, and to add water-soluble ethylene glycol, propylene glycol, glycerin or the like in order to release the diarylamine compound represented by the formula (X) by pouring the reaction product into water, and then, further neutralizing it with hydrochloric acid or the like.

After completing the hydrolysis reaction, the reaction product is poured into water and further neutralized with hydrochloric acid or the like, whereby the diarylamine represented by the formula (X) is released, and then, the resulting product is washed sufficiently and dissolved into a suitable solvent according to necessity. Thereafter, either the solution is purified with silica gel, alumina, activated clay, activated charcoal, a column or the like, or a treatment in which, for example, any of these adsorbents is added to the solution to adsorb undesired components is applied, and further, similar operations may be conducted after the product is recrystallized from a suitable solvent such as acetone, ethanol, ethyl acetate, or toluene to purify it, or the product is esterified into a methyl ester, an ethyl ester or the like.

Then, the coupling reaction of the diarylamine compound represented by the formula (X) obtained as described above and the halogen compound represented by the formula (XI) is conducted with a copper catalyst, and then, the reaction product is esterified into a methyl ester, an ethyl ester or the like, whereby the compound represented by the formula (I) may be obtained. Otherwise, the diarylamine compound represented by the formula (X) is esterified into a methyl ester, an ethyl ester or the like, and then, the coupling reaction of the resulting ester and the dihalogen compound represented by the formula (XI) with a copper catalyst, whereby the compound represented by the formula (I) may also be obtained.

In the coupling reaction of the diarylamine compound represented by the above-described formula (X) and the halogen compound represented by the formula (XI), when a halogen di-substituent is used as the compound represented by the formula (XI), preferably from 1.5 to 5 equivalents of and more preferably from 1.7 to 4 equivalents of the dihalogen compound represented by the formula (XI) are used with respect to 1 equivalent of the compound represented by the formula (X).

A copper powder, copper oxide, copper sulfate or the like may be used as the copper catalyst; and preferably from 0.001 to 3 parts by mass of and more preferably from 0.01 to 2 parts by mass of the copper catalyst are used with respect to 1 part by mass of the diarylamine compound represented by the formula (X).

Potassium phosphate, sodium carbonate, potassium carbonate or the like may be used as the base; and preferably from 1 to 6 equivalents of, and more preferably from 1.4 to 4 equivalents of the base are used with respect to 1 equivalent of the compound represented by the formula (X).

Although the solvent is used as occasion demands, a preferred example thereof includes a water-insoluble hydrocarbon system solvent having a high boiling point such as n-tridecane, tetrarine, p-cymen, and terpinolene; or a halogen system solvent having, a high boiling point such as o-dichlorobenzene, and chlorobenzene. Preferably from 0.1 to 3 parts by mass, and more preferably from 0.2 to 2 parts by mass of the solvent are used with respect to 1 part by mass of the diarylamine compound represented by the formula (X). It is preferred to implement the reaction under an inert gas such as nitrogen and argon atmosphere at a temperature preferably from 100° C. to 300° C., more preferably from 150° C. to 270° C., and still further preferably from 180° C. to 250° C. while the reaction mixture is sufficiently agitated efficiently, and further to react the mixture while the water produced during the reaction is removed.

After completing the reaction, the reaction product is dissolved into a solvent such as toluene. Isopar, and n-tridecane, and undesired substances are removed by rinsing or filtration according to need. Further, either a treatment of column purification by the use of silica gel, alumina, activated clay, activated charcoal or the like, or a treatment of adsorption of undesired components by adding any of these adsorbents to the solvent is applied. In addition, the reaction product is recrystallized from a suitable solvent such as ethanol, ethyl acetate, and toluene to purify the product.

When a halogen mono-substituent is applied as the compound represented by the formula (XI) to be used in the coupling reaction, the halogen compound represented by the formula (XI), a copper catalyst, and the base are used, and the solvent is used according to need. A copper powder, copper oxide, copper sulfate or the like may be used as the copper catalyst; and preferably from 0.001 to 3 parts by mass, and more preferably from 0.01 to 2 parts by mass of the copper catalyst are used with respect to 1 part by mass of the diarylamine compound represented by the formula (X).

Potassium phosphate, sodium carbonate, potassium carbonate or the like may be used as the base; and from 0.5 to 3 equivalents, and preferably from 0.7 to 2 equivalents of the base are used with respect to 1 equivalent of the diarylamine compound represented by the formula (X). An example of the solvent includes a water-insoluble hydrocarbon system solvent having a high boiling point such as n-tridecane, tetrarine, p-cymen, and terpinolene, or a halogen system solvent having a high boiling point such as o-dichlorobenzene, and chlorobenzene: and preferably from 0.1 to 3 parts by mass, and more preferably from 0.2 to 2 parts by mass of the solvent is used with respect to 1 part by mass of the diarylamine compound represented by the formula (X).

The following treatments and purification in the reaction may be carried out by the same manner as that of the case wherein the compound represented by the formula (XI) is halogen di-substituents.

The quinoxaline-containing compound represented by the formula (I) in the exemplary embodiment may also be synthesized in amination reaction wherein a palladium catalyst is used.

Namely, in a synthesizing method for the quinoxaline-containing, compound represented by the formula (I), the diarylamine compound represented by the formula (X) is reacted with the dihalogen compound represented by the formula (XI) in the presence of tertiary phosphines, a palladium compound, and a base, whereby the quinoline-containing compound may be synthesized.

An amount applied of the diarylamine represented by the formula (X) is in a range of usually from 0.5 to 4.0, and more preferably from 0.8 to 2.0 in a molar ratio with respect to the dihalogen compound represented by the formula (XI).

The tertiary phosphines are not specifically limited; and an example thereof includes tertiary alkyl phosphines such as triphenylphosphine, tri (tertiary butyl) phosphine, tri (p-tolyl) phosphine, tri (m-tolyl) phosphine, triisobutylphosphine, tricyclohexylphosphine, and triisopropyl phosphine. Among others, tri (tertiary butyl) phosphine is preferred. Although an amount applied of a tertiary phosphine is not specifically restricted, it is suitable in a range of from 0.5 to 10 times molar with respect to a palladium compound, and more preferable is in a range of from 2.0 to 8.0 times molar or less with respect to a palladium compound.

The palladium compounds are not specifically limited, and an example thereof includes divalent palladium compounds such as palladium acetate (II), palladium chloride (II), palladium bromide (II), and palladium trifluoroacetate (II); and zero-valent palladium compounds such as tris(dibenzylidene acetone)dipalladium (0), (dibenzylidene acetone)dipalladium (0), tetrakis(triphenylphosphine)palladium (0), and palladium-carbon. Among, others, palladium acetate and tris-dibenzylidene acetone dipalladium (0) are particularly preferable. Although an amount applied of the palladium compound is not specifically limited, it is from 0.001 to 10 mol % converted into palladium, and more preferably from 0.01 to 5.0 mol % converted into palladium with respect to the formula (XI).

The base is not specifically limited, and an example thereof includes potassium carbonate, rubidium carbonate, cesium carbonate, sodium carbonate, potassium bicarbonate, sodium bicarbonate, potassium tertiary butoxide, sodium tertiary butoxide, sodium metal, potassium metal, and hydrogenated potassium; and preferable are rubidium carbonate, and sodium tertiary butoxide. An amount applied of the base is in a range of from 0.5 to 4.0, and more preferably in a range of from 1.0 to 2.5 in a molar ratio with respect to the compound represented by the formula (XI).

The foregoing amination reaction is usually executed in an inert solvent. The solvent which may be used is any solvent so far as the present reaction is not significantly hindered; and an example thereof includes aromatic hydrocarbon solvents such as benzene, toluene, xylene, and mesitylene; and ether solvents such as diethylether, tetrahydrofuran, and dioxane; acetonitrile; dimethylformamide; and dimethylsulfoxide. Among others, aromatic hydrocarbon solvents such as toluene, and xylene are more preferable.

The amination reaction is executed under normal pressures, nitrogen and argon in an inert gas atmosphere, however the reaction may also be executed under a pressure condition. Although the reaction is conducted at the temperature in a range of from 20° C. to 300° C., and more preferable is in a range of from 50° C. to 180° C. The reaction time varies dependent on a reaction condition, and it may be selected in a range of from several minutes or more to 20 hours or less.

After the reaction, the reaction solution is poured into water, thereafter the mixture is well stirred, and the reaction product is filtered out by means of suction filtration to obtain a crude product in the case where the reaction product is a crystal. In the case where the reaction product is an oily substance, the reaction product may be extracted with a suitable solvent such as ethyl acetate, and toluene to obtain a crude product.

The crude product thus obtained is subjected to either a column purification with the use of silica gel, alumina, activated clay, activated charcoal or the like, or such a treatment that any of the adsorbents enumerated above is added into the solution, and undesired components is adsorbed by the adsorbent. In addition, when the reaction product is in a crystal state, the reaction product is recrystallized from a suitable solvent such as hexane, methanol, acetone, ethanol, ethyl acetate and toluene to purify it.

The polymers of the exemplary embodiment represented by the formula (II) may be synthesized by polymerizing the monomer represented by the following formula (XII) in accordance with a known method as described, for example, in the 4th Edition, Lecture of Experimental Chemistry, vol. 28 (compiled by the Chemical Society of Japan and published from Maruzen Co., Ltd.) and the like literary documents.

Although a reaction temperature may be arbitrarily set up, it is preferred to react with the reactants at the boiling point of the solvent used in order to remove the water produced during the polymerization. After the reaction, the reaction product is dissolved into a soluble solvent in the case where no solvent is used in the reaction. On the other hand, when any solvent is used in the reaction, the reaction solution, as it is, is dropped into a poor solvent of alcohols such as methanol, and ethanol as well as acetone and the like in which the polymer is hardly dissolved to precipitate the polymer. After separating the polymer, it is washed sufficiently with water or an organic solvent and dried. Moreover, such reprecipitation treatment that the resulting polymer is dissolved into an appropriate organic solvent, and the solution is dropped into a poor solvent to precipitate a fresh polymer may be repeated, if necessary.

In case of the reprecipitation treatment, it is preferred to implement the treatment while the mixture is stirred efficiently by means of a mechanical stirrer and the like. The

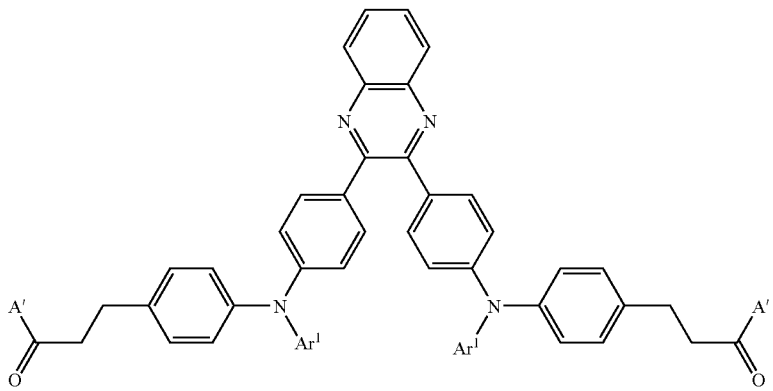

(XII)

wherein $Ar^1$ is the same as the $Ar^1$ in the above-described formula (I), A' is a hydroxyl group, a halogen atom, or a group —O—$R^6$ (wherein $R^6$ is a substituted or unsubstituted alkyl group, a substituted or unsubstituted aryl group, or a substituted or unsubstituted aralkyl group).

Namely, the quinoxaline-containing compound polymers represented by the formula (II) may be synthesized by the following manners.

<1> In Case where A' is a Hydroxyl Group:

In the case where A' is a hydroxyl group, substantially equivalent amounts of the dihydric alcohols represented by HO—(Y—O)$_m$—H (wherein Y and m have the same meanings as the Y and the m represented by the foregoing formula (II); and the definition is the same as that of the following cases <2> and <3>) and the monomer are mixed with each other, and the mixture is polymerized by the use of an acid catalyst. As the acid catalyst, those which are used in a usual esterification reaction may be applied. An example thereof includes sulfuric acid, toluenesulfonic acid, trifluoroacetic acid and the like; and it may be used in a range of from preferably 1/10,000 to 1/10 parts by mass, and more preferably 1/1,000 to 1/50 parts by mass with respect to 1 part by mass of a monomer.

In order to remove the water produced during the synthesis, it is preferred to use a solvent capable of azeotropic with water; an effective example thereof includes toluene, chlorobenzene, 1-chloronaphthalene or the like. It may be used in a range of from preferably 1 to 100, and more preferably 2 to 50 parts by mass with respect to 1 part by mass of a monomer.

solvent used for dissolving the polymer in case of the reprecipitation treatment is used in a range of preferably from 1 to 100 parts by mass, and more preferably from 2 to 50 parts by mass with respect to 1 part by mass of a polymer. Meanwhile, the poor polymer may be used in a range of from 1 to 1,000 parts by mass, and more preferably 10 to 500 parts by mass with respect to 1 part by mass of a polymer.

<2> In Case where A' is a Halogen:

In the case where A' is a halogen, substantially equivalent amounts of the dihydric alcohols represented by HO—(Y—O)$_m$—H and the monomer are mixed with each other, and the mixture is polymerized by the use of an organic base catalyst such as pyridine, and triethylamine. The organic base catalyst may be used in a range of from 1 to 10 equivalent, and more preferably 2 to 5 part by mass with respect to 1 equivalent of a monomer.

An efficient example of the solvent includes methylene chloride, tetrahydrofuran (THF), toluene, chlorobenzene, 1-chloronaphthalene and the like; and it may be used in a range of from 1 to 100 parts by mass, and preferably from 2 to 50 parts by mass with respect to 1 part by mass of a monomer. The reaction temperature may be arbitrarily set up. After the polymerization, the reprecipitation treatment is conducted as mentioned above, and the resulting product is purified.

In case of the dihydric alcohols such as bisphenol or the like having high acidity, an interfacial polymerization process may be applied. Namely, the polymerization may be accomplished in such that water is added to any of the dihydric alcohols, an equivalent of a base is added thereto to dissolve the mixture, and then, the dihydric alcohol and an equivalent of a monomer solution are added while the mixture is agitated vigorously, whereby a polymer is obtained. In this case, water is used in a range of from 1 to 1,000, and preferably from 2 to 500 parts by mass with respect to 1 part by mass of the dihydric alcohol. An effective example of the solvent which dissolves a monomer includes methylene chloride, dichloroethane, trichloroethane, toluene, chlorobenzene, 1-chloronaphthalene and the like.

The reaction temperature may be set up arbitrarily; and it is effective to use a phase-transfer catalyst such as an ammonium salt, and a sulfonium salt to promote the reaction. The phase-transfer catalyst may be used in a range of from 0.1 to 10 parts by mass, and preferably 0.2 to 5 parts by mass with respect to 1 part by mass of a monomer.

<3> In Case where A' is —O—$R^6$

In the case where A' is —O—$R^6$, a polymer may be synthesized by such a manner that excess of any of the dihydric alcohols represented by HO—(Y—O)$_m$—H is added to a monomer, a catalyst of inorganic acids such as sulfuric acid and phosphoric acid; titanium alkoxides; acetates or carbonates of calcium, cobalt or the like; or oxides of zinc is used, and the mixture is heated, whereby the polymer is obtained through transesterification.

A dihydric alcohol may be used in a range of from 2 to 100, and preferably 3 to 50 equivalents with respect to 1 equivalent of a monomer. A catalyst may be used in a range of from 1/1,000 to 1, and preferably 1/100 to 1/2 part by mass with respect to 1 part by mass of a monomer.

The reaction is carried out at a reaction temperature of from 200° C. to 300° C. After completing the transesterification from the group —O—$R^6$ to the group HO—(Y—O)$_m$—H, it is preferred to react the reactants under a reduced pressure in order to promote the polymerization reaction due to desorption of the group HO—(Y—O)$_m$—H. Furthermore, the reaction may also be conducted in such a manner that a high-boiling point solvent such as 1-chloronaphthalene capable of azeotropic with the group HO—(Y—O)$_m$—H is used to react with the reactants under a reduced pressure while the group HO—(Y—O)$_m$—H is removed by means of the azeotropy.

The quinoxaline-containing compound and the quinoxaline-containing compound polymer according to the exemplary embodiment exhibit excellent charge transportability, solubility control due to an alkyl ester group, film formability due to the polymer, and high charge injection property. The quinoxaline-containing compound and the quinoxaline-containing compound polymer of the exemplary embodiment may also be easily synthesized; and they are also possible to control physical properties of ionized potential (IP), glass transition temperature (Tg) and the like by introducing substituents. Accordingly, they are very useful compounds used for a material of organic electronic devices such as organic photoreceptors, organic electroluminescence elements, organic solar batteries, organic transistors and the like.

A variety of properties such as solubility, film forming property, mobility, heat resistance, matching of the oxidation potential with the electrode couple and the like is required for a charge transporting material. In order to satisfy these requirements, it is generally practiced to introduce substituents, whereby the physical properties are controlled. Moreover, since the physical properties of a charge transporting polymer have high correlativity with the physical properties of the charge transporting monomer being a raw material, a molecular design of a low-molecular compound becomes important. The monomer being a raw material of known triarylamine polymers may be classified broadly into the following two categories.

(1) Dihydroxyarylamine
(2) Bishydroxyalkylarylamine

However, since the dihydroxyarylamine of (1) has an aminophenol structure, it is easily oxidized and difficult to purify it. Particularly, when it is in a parahydroxy-substituted structure, it becomes further unstable. In addition, since the questioned compound has a structure wherein oxygen is directly substituted in an aromatic ring, there is such a problem that a deflection appears easily in the electric charge distribution due to the electron-drawing thereof, so that its mobility decreases easily.

On the other hand, although the bishydroxyalkylarylamine of (2) has less influence of the electron-drawing of oxygen due to methylene group, the synthesis of the monomer thereof is difficult. Namely, since both bromine and iodine are reactive, the resulting product becomes easily a mixture in the reaction of diarylamine or diarylbenzidine and bromoiodebenzene, so that it results in decrease of the yield. Furthermore, there is such a problem that alkyllithium to be used in lithination of bromine, and ethylene oxide are dangerous and have high toxicity, so that a careful handling thereof is required.

The organic electroluminescence element prepared by using the π-conjugated system polymer represented by known paraphenylenevinylene, and the polymer wherein triphenylamine is introduced to a side chain of polyphosphazene involves problems in color tone, luminescence intensity, durability and the like.

Accordingly, for the sake of developing an organic electron device such as the organic electroluminescence element and the like having a higher emission luminance and being excellent in stability in case of repeated use, an organic electron material which is easily synthesized and has high charge transportability as well as excellent luminescence property has been desired.

EXAMPLES

In the following, the present invention is described in accordance with examples, however it is to be noted that the invention is not restricted to these examples.

Example 1

Acetanilide (25.0 g), methyl 4-iodophenylpropionate (64.4 g), potassium carbonate (38.3 g), copper sulfate pentahydrate (2.3 g), and n-tridecane (50 ml) are placed into a three-necked flask having 500 ml capacity, and the mixture is heated and agitated under nitrogen stream at 230° C. for 20 hours. After completing the reaction, the solution prepared by dissolving potassium hydroxide (15.6 g) into ethylene glycol (300 ml) is added to the reaction product, the mixture is heated to reflux under nitrogen stream for 3.5 hours, then the temperature thereof is cooled to a room temperature, the reaction solution is poured into 1 L of distilled water, and the solution is neutralized with hydrochloric acid to separate out a crystal. The crystal is filtered by suction filtration, the resulting product is washed sufficiently with water, and then the product is sifted into a 1 L flask.

Toluene (500 ml) is added to the 1 L flask, the mixture is heated to reflux, and water is removed by means of azeotrope. Thereafter, a methanol solution (300 ml) of concentrated sulfuric acid (1.5 ml) is added to the product, and heated to reflux under nitrogen stream for 5 hours. After the reaction, the reaction product is extracted with toluene, and the organic layer is washed sufficiently with distilled water. Then, the resulting product is dried with anhydrous sodium sulfate, thereafter the solvent is distilled off under a reduced pressure, and the product is recrystallized from hexane, thereby to obtain 36.5 g of diarylamine (DAA-1).

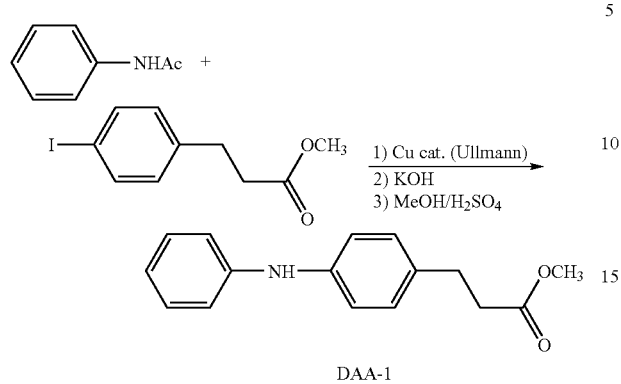

DAA-1

Synthesis of Quinoxaline Dihalide Member (Intermediate 1)

1,2-Phenylenediamine (2.9 g), and 4,4'-dibromobenzyl (11 g) are placed into a three-necked flask having 500 ml capacity and provided with a thermometer, a condenser, and a magnetic stirrer, and the mixture is dissolved into 200 ml of isopropylether. The solution is heated to reflux at a room temperature for 1 hour while the solution is magnetically stirred. It is confirmed by means of TLC (hexane/ethyl acetate=3/1) that the spots of 1,2-phenylenediamine disappear, and then, the product is cooled to a room temperature. Since a crystal separates out during the reaction, it is filtered by means of suction filtration. The crystal is further washed with 50 ml of methanol, and then the crystal is subjected to vacuum drying at 70° C. for 15 hours to obtain 10 g of the [intermediate 1].

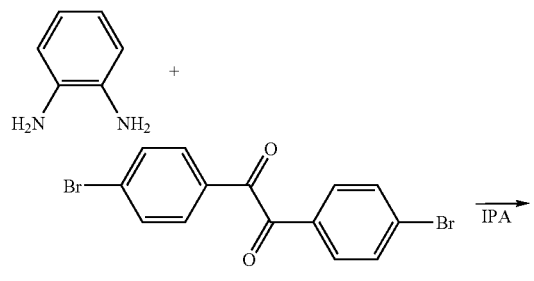

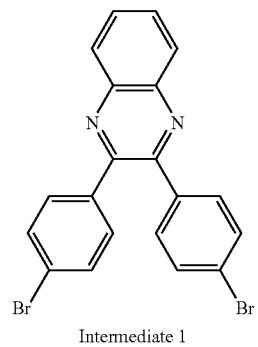

Intermediate 1

DAA-1 (8.0 g), [intermediate 1] (6.3 g), palladium acetate (II) (150 mg), and rubidium carbonate (19.6 g) are placed into a three-necked flask having 200 ml capacity and provided with a thermometer, a condenser, and a magnetic stirrer, and the mixture is dissolved into 50 ml of xylene. Tritertiarybutylphosphine (420 mg) is added rapidly to the solution, and heated to reflux under nitrogen atmosphere for 9 hours while the mixture is magnetically stirred.

It is confirmed by means of TLC (hexane/ethyl acetate 3/1) that the spots of the [intermediate 1] disappear, and then, the product is cooled to a room temperature. After removing inorganic substances by means of Celite suction filtration, the resulting product is washed with 100 ml of dilute hydrochloric acid, 200 ml×3 of water, and 200 ml×1 of saturated saline in this order until the product is neutralized. After drying the product with anhydrous sodium sulfate, purification is made by means of silica gel chromatography (hexane/ethyl acetate 3/1), and then, vacuum drying is conducted at 70° C. for 15 hours to obtain 5.2 g of an exemplified compound [2] (46% yield).

Figure 2:
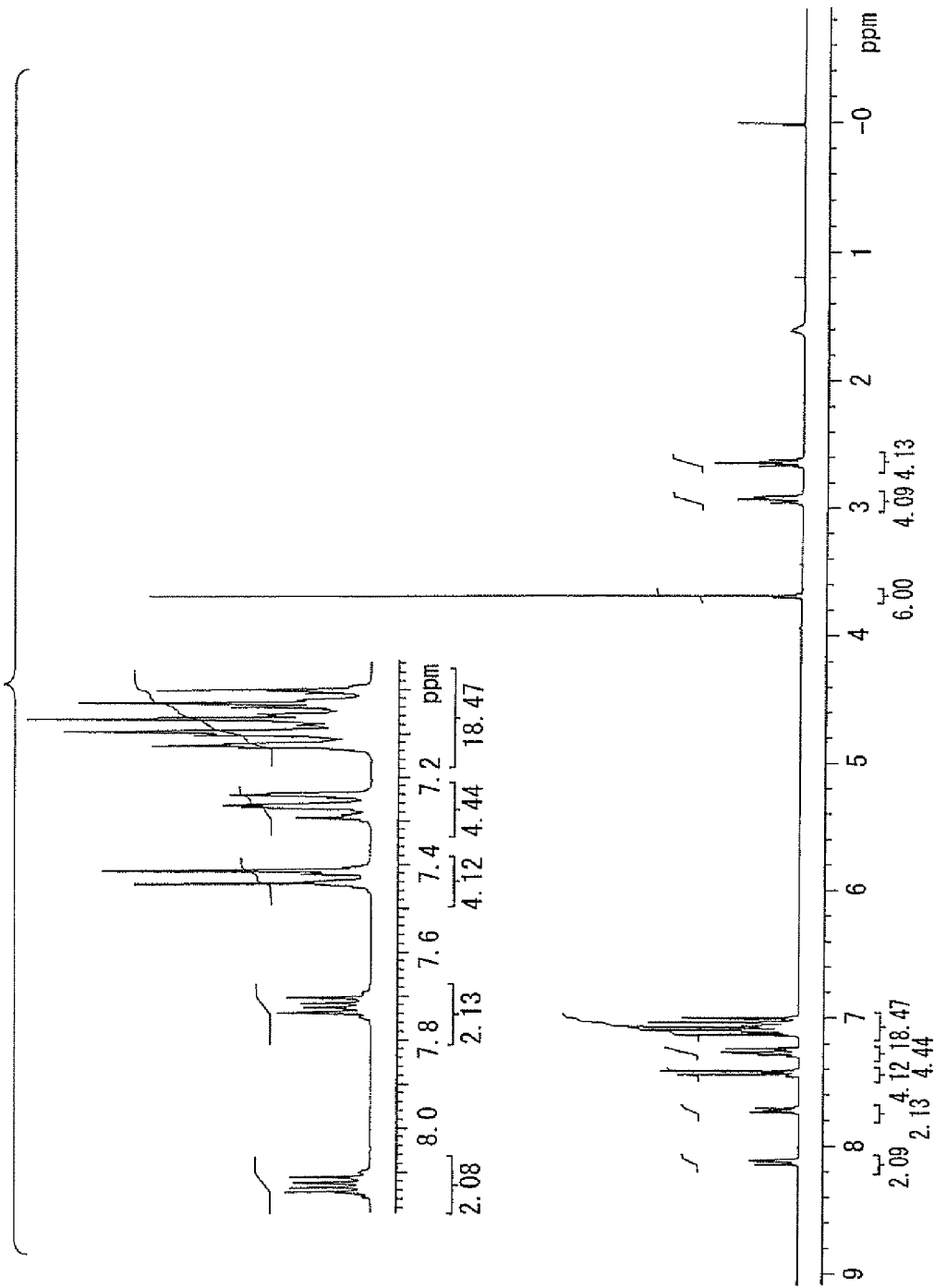
FIG. 2 is the NMR spectrum of the compound obtained by example 1.

The melting point of the exemplified compound [2] is 135 to 136° C. The infrared absorption spectrum of the resulting exemplified compound [2] is shown in FIG. 1, and the NMR spectrum ($^1$H-NMR, solvent: $CDCl_3$) is shown in FIG. 2.

NMR spectrum data: δ 2.6 (ppm)(t, 4H, $CH_2$), δ 2.9 (ppm) (t, 4H, $CH_2$), δ 3.7 (ppm)(s, 6H, $CH_3$) δ 7.0-7.16 (ppm)(m, 18H, Ar), δ 7.26 (ppm)(t, 4H, Ar), δ 7.43 (ppm)(d, 4H, Ar) δ 7.43)(ppm)(d, 4H, Ar) δ 7.72 (ppm)(dd, 2H, Ar), δ 8.12 (ppm)(dd, 2H, Ar)

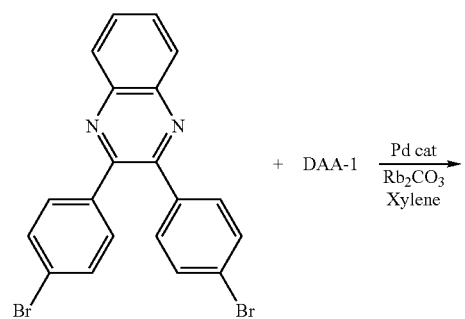

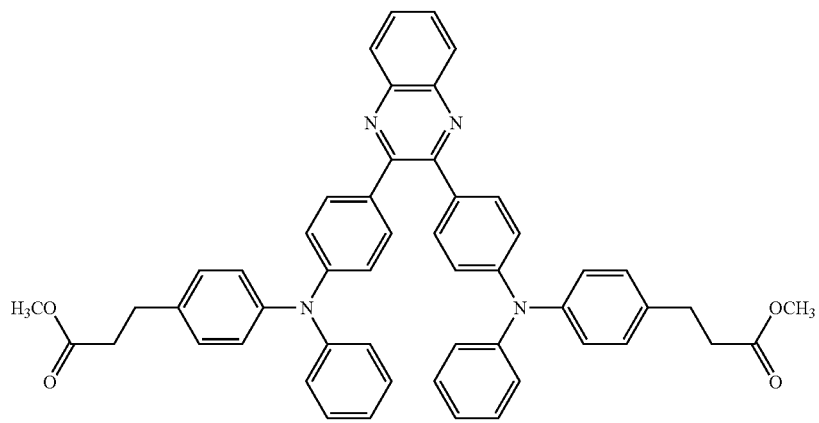

Example 2

4-Phenylacetanilide (4.0 g), methyl 4-iodophenylpropionate (6.4 g), potassium carbonate (3.9 g) and copper sulfate pentahydrate (0.40 g) are placed into a three-necked flask having 100 ml capacity and provided with a thermometer, a condenser, and a magnetic stirrer, and the mixture is dissolved into o-dichlorobenzene (20 ml). The solution is heated and agitated under nitrogen atmosphere at 185° C. for 13 hours. After completing the reaction, the solution prepared by dissolving potassium hydroxide (1.3 g) into ethylene glycol (25 ml) is added to the reaction product, the mixture is heated to reflux under nitrogen atmosphere for 5 hours. After completing the reaction, the temperature thereof is cooled to a room temperature, the reaction solution is poured into water (200 ml), and the solution is neutralized with hydrochloric acid to separate out a crystal. The crystal is filtered, the resulting product is washed sufficiently with water, and then the product is sifted into a 1 L flask.

Toluene (300 ml) is added to the 1 L flask, the mixture is heated to reflux, and water is removed by means of azeotrope. Thereafter, methanol (100 ml) and concentrated sulfuric acid (0.5 ml) are added to the product, and heated to reflux under nitrogen stream for 3 hours. After the reaction, the reaction product is poured into distilled water and extracted with toluene, and the toluene layer is washed sufficiently with distilled water. Then, the resulting product is dried with anhydrous sodium sulfate, thereafter the solvent is distilled off under a reduced pressure, and the product is recrystallized from an ethyl acetate/hexane mixed solution, thereby to obtain 3.2 g of diarylamine (DAA-2).

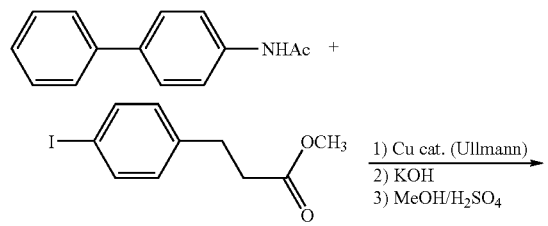

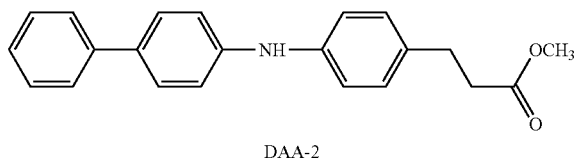

DAA-2

DAA-2 (2.1 g), [intermediate 1] (1.4 g), palladium acetate (II) (36 mg) and rubidium carbonate (4.4 g) are placed into a three-necked flask having 200 ml capacity and provided with a thermometer, a condenser, and a magnetic stirrer, and the mixture is dissolved into 30 ml of xylene. Tritertiarybutylphosphine (97 mg) is added rapidly to the solution, and heated to reflux under nitrogen atmosphere for 5 hours while the mixture is magnetically stirred.

It is confirmed by means of TLC (hexane/ethyl acetate=3/1) that the spots of the [intermediate 1] disappear, and then, the product is cooled to a room temperature. After removing inorganic substances by means of Celite suction filtration, the resulting product is washed with 20 ml of dilute hydrochloric acid, 50 ml×3 of water, and 50 ml×1 of saturated saline in this order until the product is neutralized. After drying the product with anhydrous sodium sulfate, boil wash is made by means of silica gel chromatography (hexane/ethyl acetate=3/1), with an acetone/methanol mixed solution, and then, vacuum drying is conducted at 70° C. for 15 hours to obtain 0.5 g of an exemplified compound [6] (17% yield).

Figure 3:
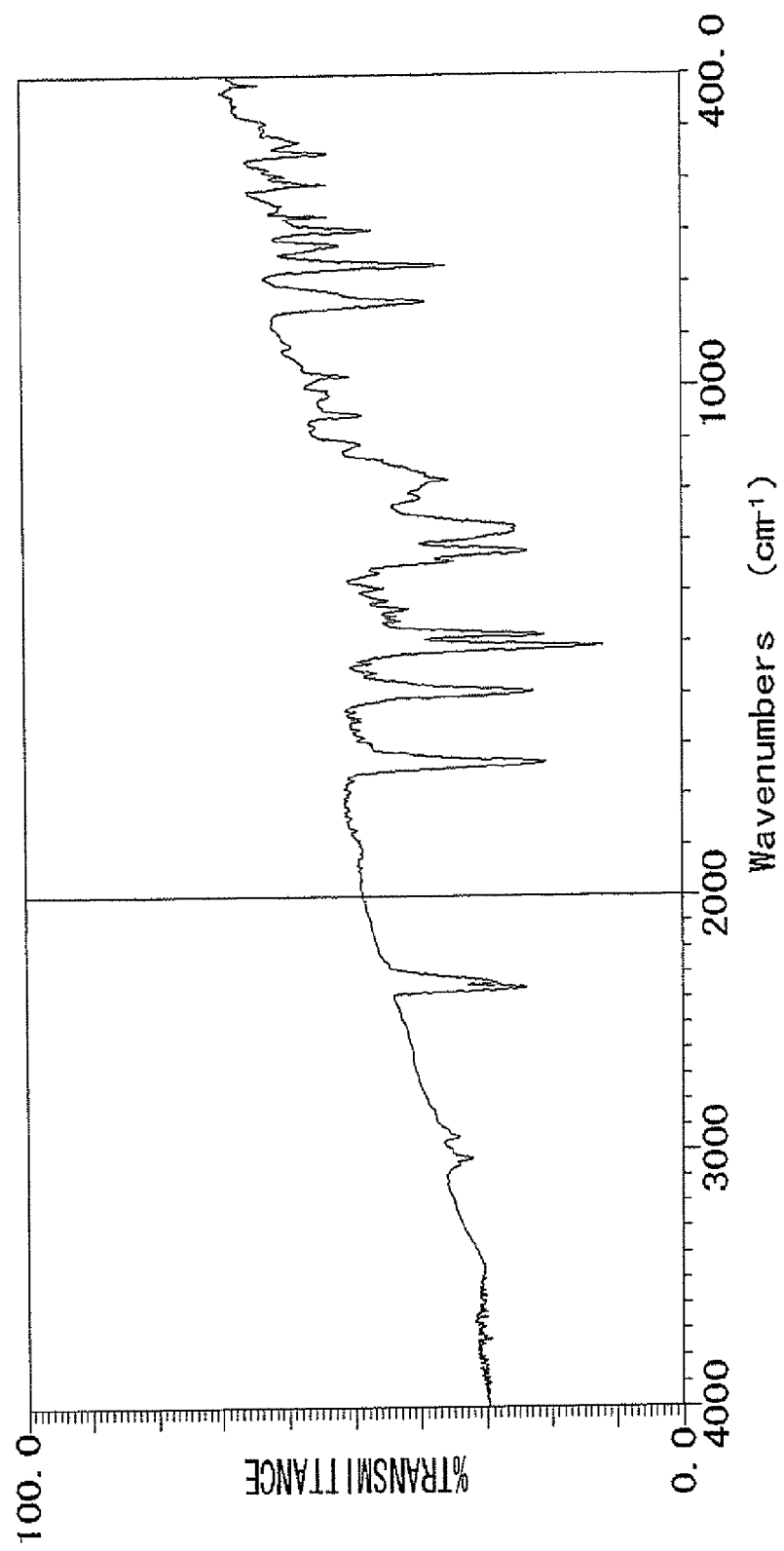
FIG. 3 is the IR spectrum of the compound obtained by example 2.
Figure 4:
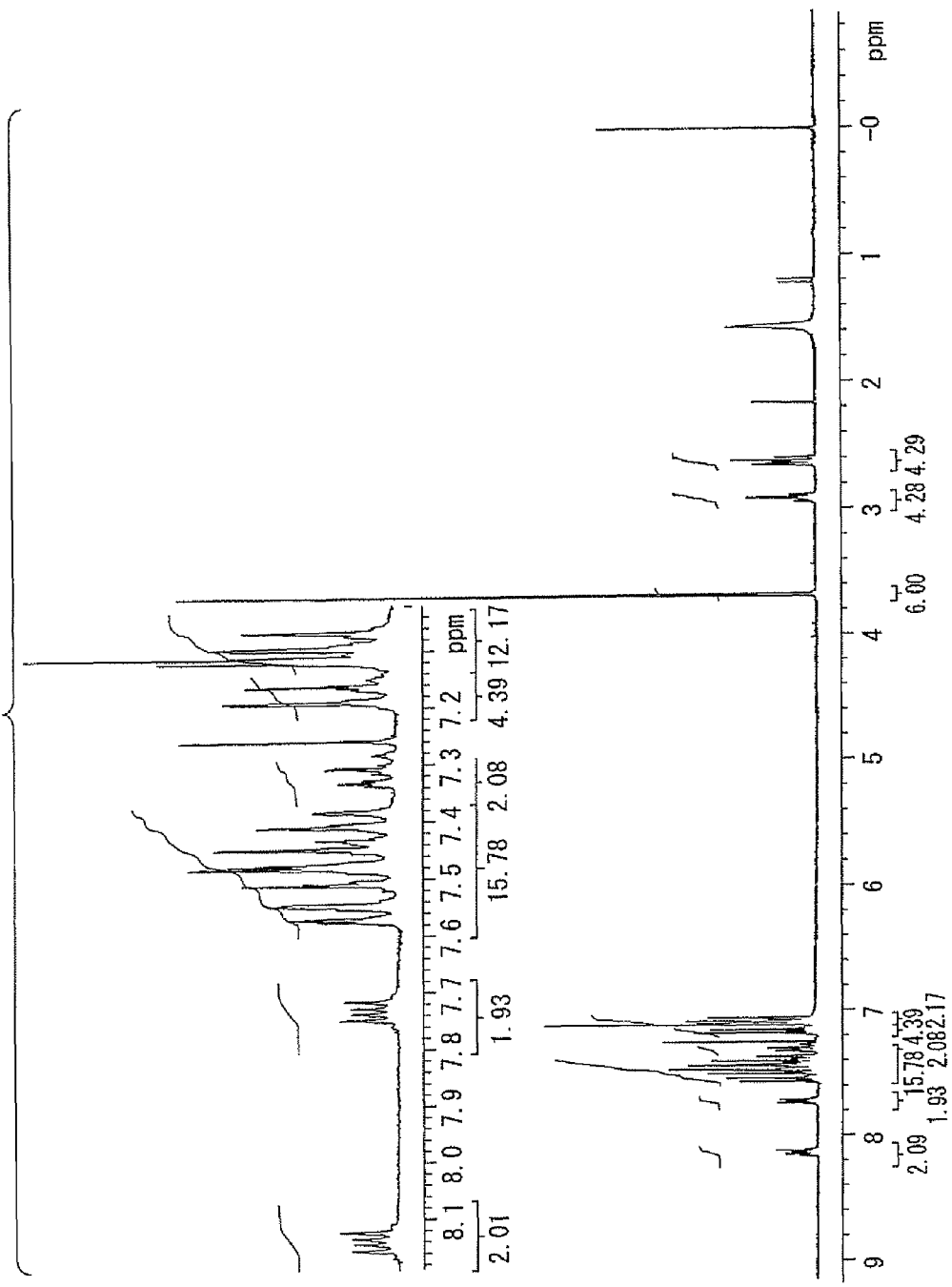
FIG. 4 is the NMR spectrum of the compound obtained by example 2.

The melting point of the exemplified compound [6] is 177 to 178° C. The infrared absorption spectrum of the resulting exemplified compound [6] is shown in FIG. 3, and the NMR spectrum ($^1$H-NMR, solvent. CDCl$_3$) is shown in FIG. 4.

NMR spectrum data: δ 2.6 (ppm)(t, 4H, CH$_1$), δ 2.9 (ppm)(t, 4H, CH$_2$), δ 3.7 (ppm)(s, 6H, CH$_3$) δ 7.06-7.14 (ppm)(m, 12H, Ar), δ 7.18 (ppm)(d, 4H, Ar), δ 7.31 (ppm)(t, 2H, Ar) δ 7.38-7.60 (ppm)(m, 16H, Ar), δ 7.73 (ppm)(dd, 2H, Ar), δ 8.14 (ppm)(dd, 2H, Ar)

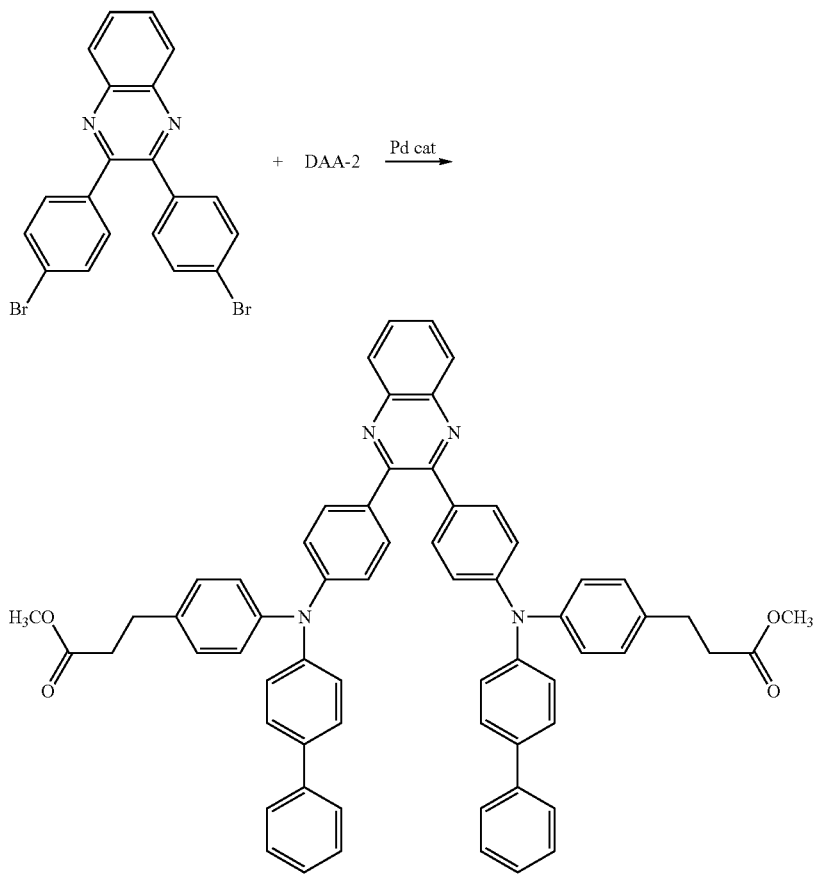

Example 3

N-(4-iodophenyl)pyrrole (16 g), methyl 3-(4-acetamidophenyl)propionate (14 g), potassium carbonate (8.3 g), and copper sulfate pentahydrate (1.3 g) are placed into a three-necked flask having 300 ml capacity and provided with a thermometer, a condenser, and a magnetic stirrer, and the mixture is dissolved into o-dichlorobenzene (50 ml). The solution is heated and agitated under nitrogen atmosphere at 180° C. for 24 hours. After completing the reaction, the solution prepared by dissolving potassium hydroxide (4.5 g) into ethylene glycol (100 ml) is added to the reaction product, the mixture is heated to reflux under nitrogen atmosphere for 4 hours. After completing the reaction, the temperature thereof is cooled to a room temperature, the reaction solution is poured into water (300 ml), and the solution is neutralized with hydrochloric acid to separate out a crystal. The crystal is filtered, the resulting product is washed sufficiently with water, and then the product is sifted into a 1 L flask.

Toluene (300 ml) is added to the 1 L flask, the mixture is heated to reflux, and water is removed by means of azeotrope. Thereafter, methanol (400 ml) and p-toluenesulfonic acid (1.0 g) are added to the product, and heated to reflux under nitrogen stream for 4 hours. After the reaction, the reaction product is poured into 1.0 L of distilled water and extracted with toluene, and the toluene layer is washed sufficiently with distilled water. Then, the resulting product is dried with anhydrous sodium sulfate, thereafter the solvent is distilled off under a reduced pressure, the resulting product is treated with 10 g of activated clay, and then the product is recrystallized from a toluene/hexane mixed solution, thereby to obtain 13 g of diarylamine (DAA-3).

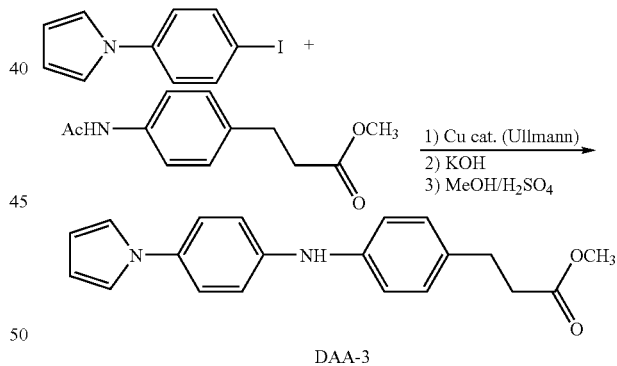

DAA-3 (1.4 g), [intermediate 1] (0.9 g), palladium acetate (II) (22 mg), and rubidium carbonate (2.8 g) are placed into a three-necked flask having 100 ml capacity and provided with a thermometer, a condenser, and a magnetic stirrer, and the mixture is dissolved into 50 ml of xylene. Tritertiarybutylphosphine (100 mg) is added rapidly to the solution, and heated to reflux under nitrogen atmosphere for 8 hours while the mixture is magnetically stirred.

It is confirmed by means of TLC (hexane/ethyl acetate 3/1) that the spots of the [intermediate 1] disappear, and then, the product is cooled to a room temperature. After removing inorganic substances by means of Celite suction filtration, the resulting product is washed with 20 ml of dilute hydrochloric acid, 50 ml×3 of water, and 50 ml×1 of saturated saline in this order until the product is neutralized. After drying the product with anhydrous sodium sulfate, the solvent is distilled off under a reduced pressure, and the product is treated with 2.0 g of activated clay, whereby impurities being color components are removed. Then, the resulting product is washed with 100 ml of methanol, and vacuum drying is conducted at 70° C. for 15 hours to obtain 1.2 g of an exemplified compound [11] (65% yield).

Figure 5:
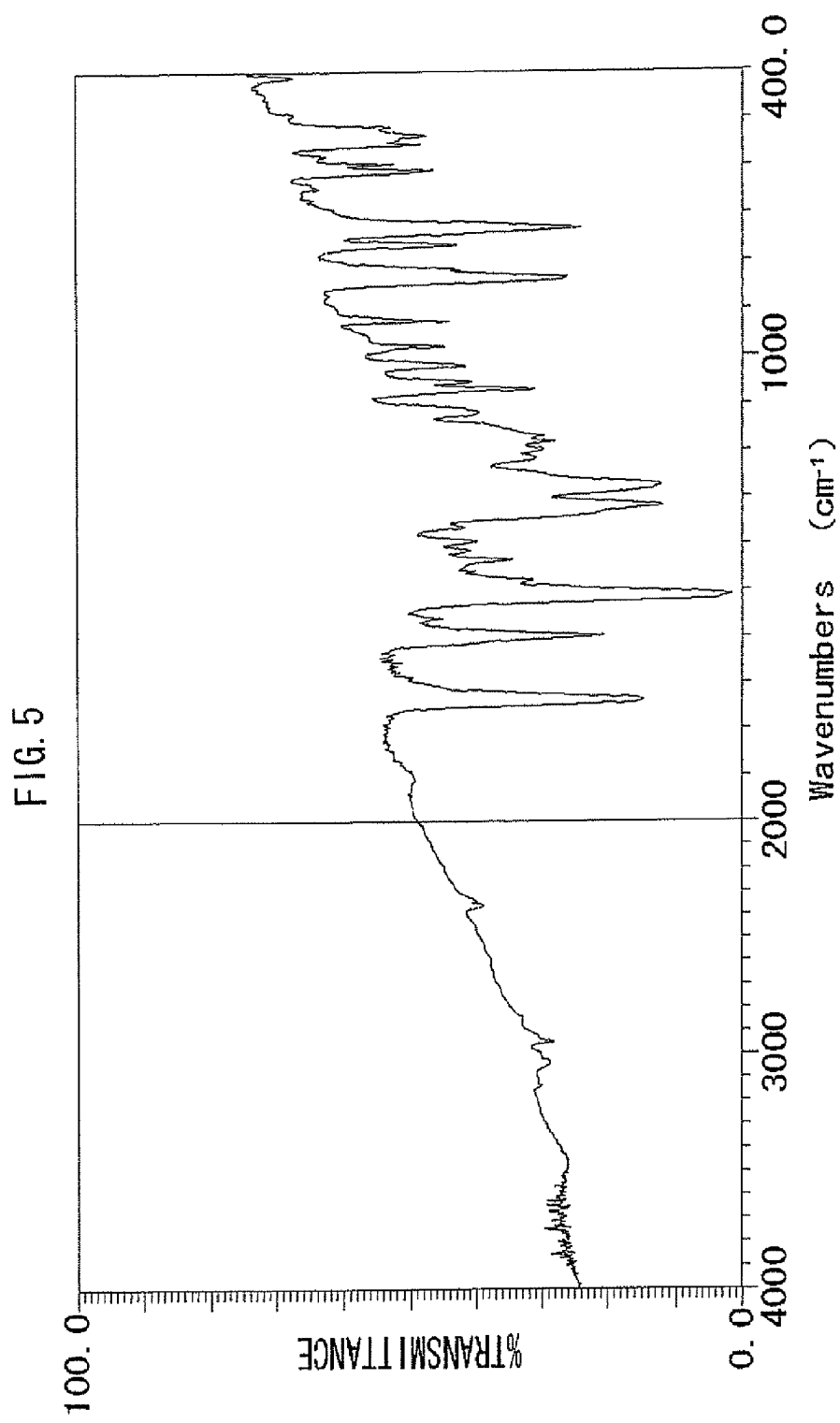
FIG. 5 is the IR spectrum of the compound obtained by example 3.
Figure 6:
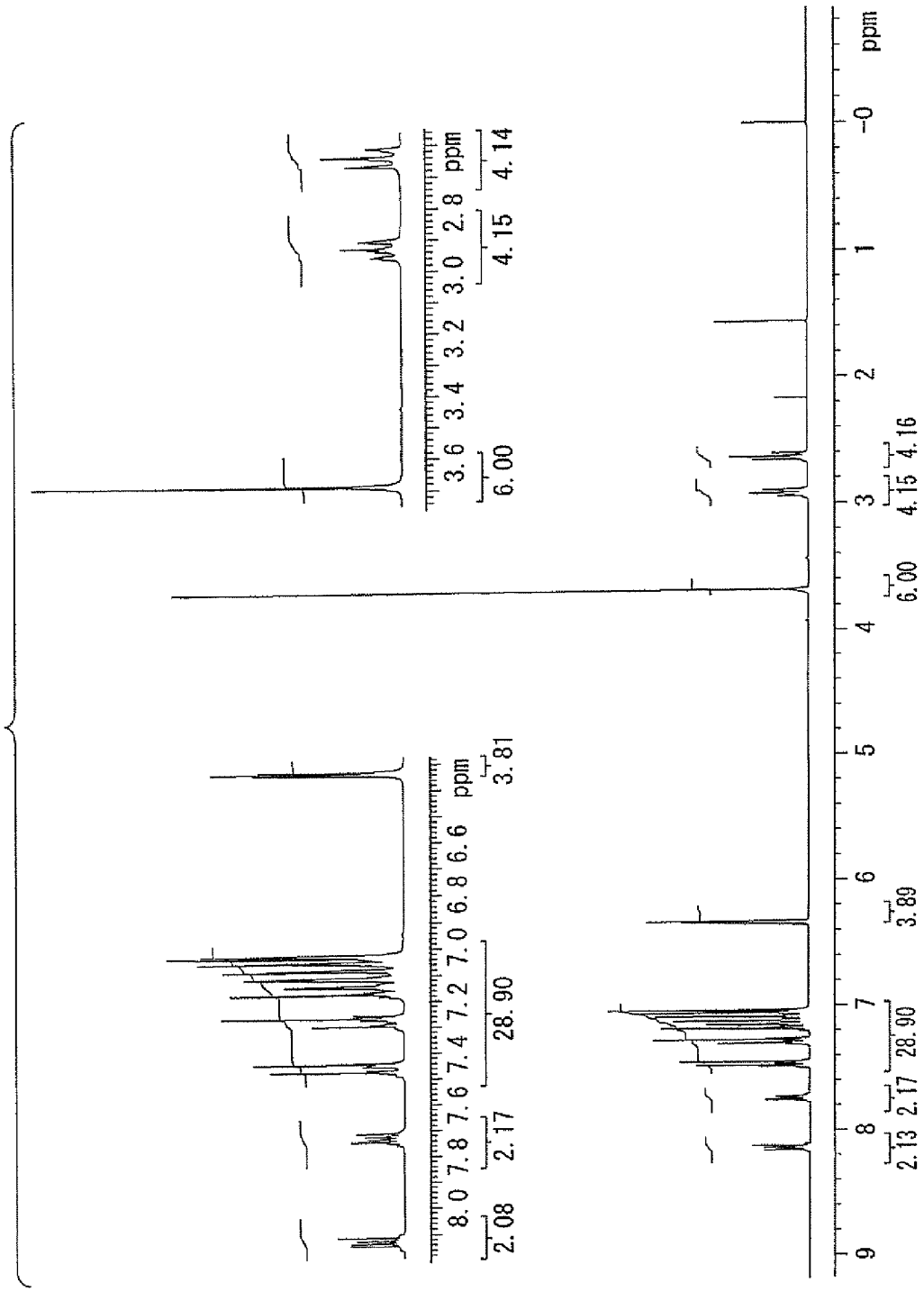
FIG. 6 is the NMR spectrum of the compound obtained by example 3.

The melting point of the exemplified compound [11] is 177 to 178° C. The infrared absorption spectrum of the resulting exemplified compound [11] is shown in FIG. 5, and the NMR spectrum ($^1$H-NMR, solvent: CDCl$_3$) is shown in FIG. 6.

NMR spectrum data: δ 2.6 (ppm)(t, 4H, CH$_2$), δ 2.9 (ppm) (t, 4H, CH$_2$), δ 3.7 (ppm)(s, 6H, CH$_3$) δ 6.34 (ppm)(s, 4H, Ar), δ 7.0-7.20 (ppm)(m, 20H, Ar), δ 7.28 (ppm)(d, 4H, Ar), δ 7.46 (ppm)(d, 4H, Ar) δ 7.74 (ppm)(dd, 2H, Ar), δ 8.14 (ppm)(dd, 2H, Ar)

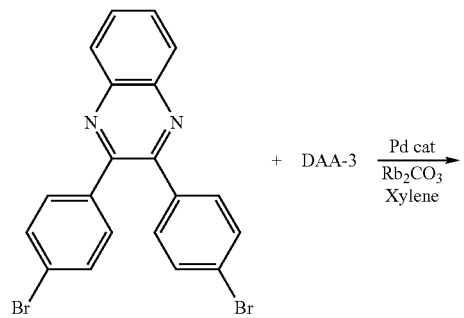

pressure is reduced to 50 Pa, the product is heated to 210° C. while ethylene glycol is distilled off, and the reaction is continued for 6 hours. Thereafter, the reaction product is cooled to a room temperature, it is dissolved into 50 ml of tetrahydrofuran, and insoluble materials are filtered by 0.5 μl of a polytetrafuloroethylene (PTFE) filter, and the filtrate is distilled off under a reduced pressure. Then, the resulting product is dissolved into 300 ml of monochlorobenzene, and the solution is washed with 300 ml of 1N—HCl, and 500 ml×3 of water in this order.

The monochlorobenzene solution is distilled off up to 30 ml under a reduced pressure, and it is dropped into 800 ml of ethyl acetate/methanol=1/3 to reprecipitate a polymer. The resulting polymer is filtered and washed sufficiently with methanol, and then, the polymer is vacuum-dried at 60° C. for

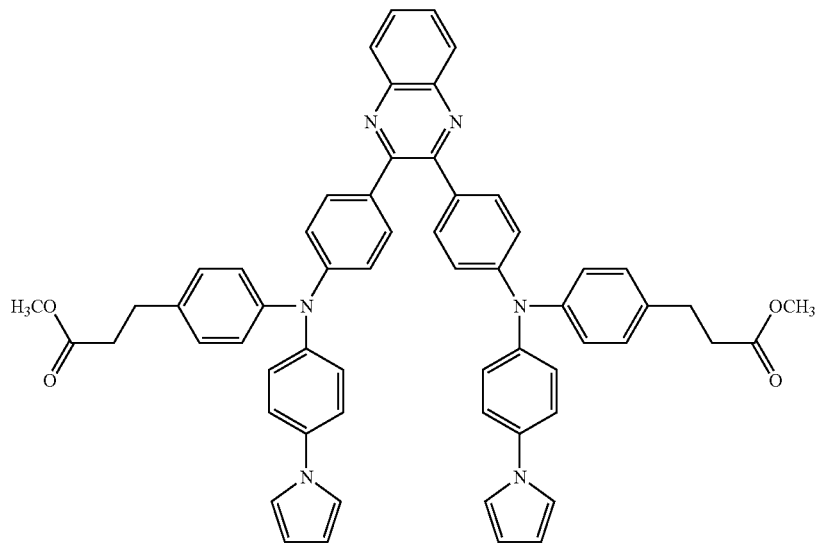

Example 4

1.5 g of the exemplified compound: [2] obtained in example 1, 10 ml of ethylene glycol, and 0.02 g of tetrabuthoxytitanium are placed into a three-necked eggplant flask having 50 ml capacity, and the mixture is heated and agitated under nitrogen atmosphere at 200° C. for 5 hours. After confirming the disappearance of the exemplified compound: [2] by means of TLC (hexane/ethyl acetate=3/1), the 16 hours to obtain 0.9 g of polymer [exemplified compound [(1)]]. As a result of measuring the molecular weight of the polymer by means of gel permeation chromatography (GPC) (trade name: HLC-8120GPC, manufactured by Tosoh Corporation), the weight average molecular weight MW=6.1× 10$^4$ (styrene basis), Mn (number average molecular weight)/ Mw (weight average molecular weight)=1.01, and the degree of polymerization p determined from the molecular weight of the monomer is about 76.

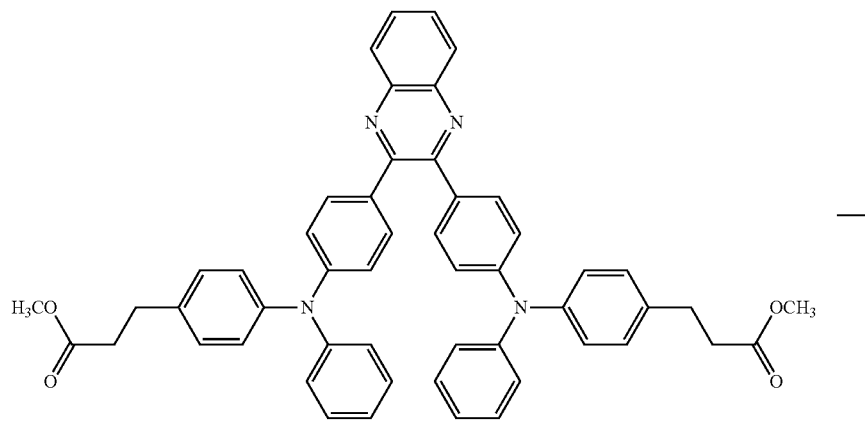

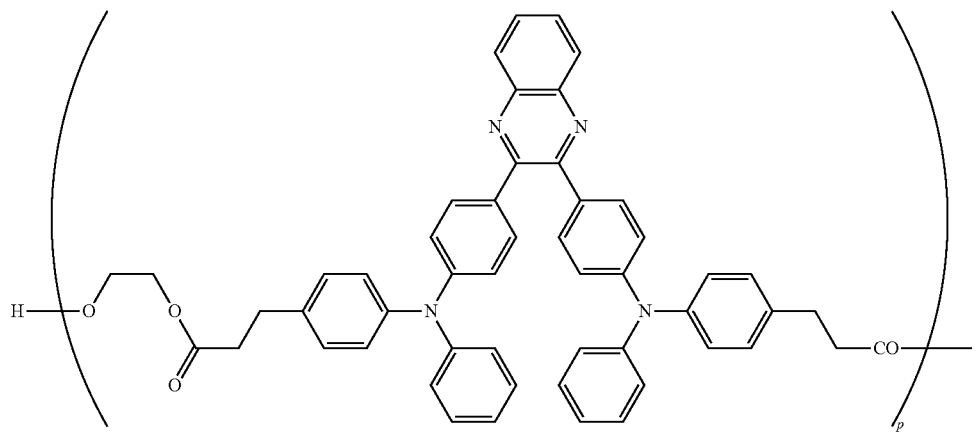

Example 5

1.0 g of the exemplified compound: [6] obtained in example 2, 10 ml of ethylene glycol, and 0.02 g of tetrabuthoxytitanium are placed into a three-necked eggplant flask having 50 ml capacity, and the mixture is heated and agitated under nitrogen stream at 200° C. for 5 hours. After confirming the disappearance of the exemplified compound: [6] by means of TLC (hexane/ethyl acetate=3/1), the pressure is reduced to 60 Pa, the product is heated to 210° C. while ethylene glycol is distilled off, and the reaction is continued for 5 hours. Thereafter, the reaction product is cooled to a room temperature, it is dissolved into 50 ml of tetrahydrofuran, and insoluble materials are filtered by 0.5 μl of a polytetrafuloroethylene (PTFE) filter, and the filtrate is distilled off under a reduced pressure. Then, the resulting product is dissolved into 200 ml of monochlorobenzene, and the solution is washed with 300 ml of 1N—HCl, and 300 ml×3 of water in this order.

The monochlorobenzene solution is distilled off up to 20 ml under a reduced pressure, and it is dropped into 800 ml of ethyl acetate/methanol=1/3 to reprecipitate a polymer. The resulting polymer is filtered and washed sufficiently with methanol, and then, the polymer is vacuum-dried at 60° C. for 15 hours to obtain 0.7 g of polymer [exemplified compound [(7)]]. As a result of measuring the molecular weight of the polymer by means of gel permeation chromatography (GPC) (trade name: HLC-8120GPC, manufactured by Tosoh Corporation), the weight average molecular weight MW=7.5×$10^4$ (styrene basis), Mn (number average molecular weight)/Mw (weight average molecular weight)=1.35, and the degree of polymerization p determined from the molecular weight of the monomer is about 79.

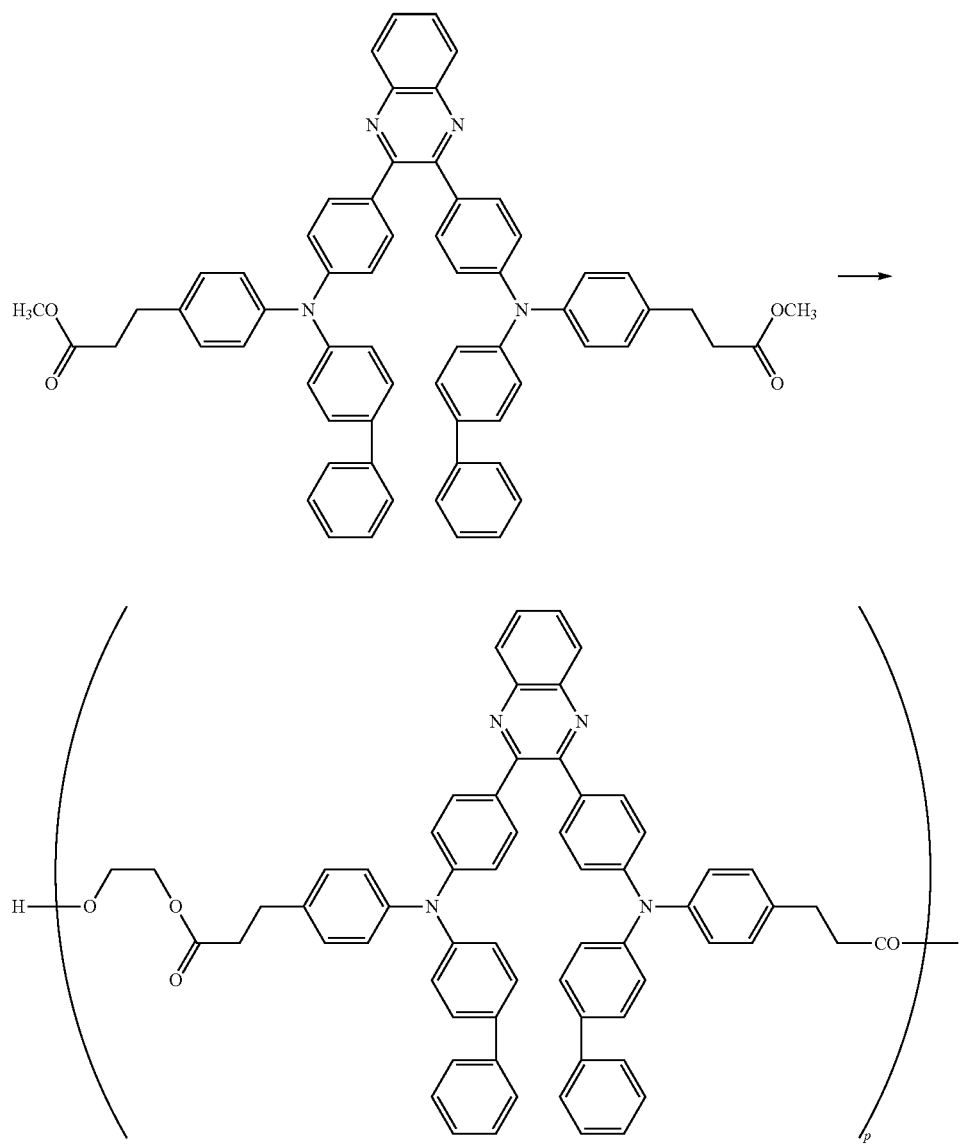

Comparative Example 1

In order to compare the quinoxaline-containing compounds and the quinoxaline-containing compound polymers according to the exemplary embodiment obtained in the foregoing examples 1 to 5, MEH-PPV ((Poly[2-methoxy-5-(2'-ethylhexyloxy)-1,4-phenylenevinylene] (weight average molecular weight=86000)) is prepared, and it is utilized as a comparative example.

Each mobility of the quinoxaline-containing compounds or the quinoxaline-containing, compound polymers according to the exemplary embodiment obtained in examples 1 to 5, and the sample of comparative example 1 is measured in accordance with Time of Flight method (trade name: TOF-401, manufactured by Optel Ltd.). Each ionization potential of them is measured by (trade name: Ac2, manufactured by Riken Ltd.). It is to be noted that in the mobility measurement, a 40% by mass dispersion film (20% by mass dispersion film is used in only example 2) with respect to polycarbonate is used in case of a monomer, if it is not specifically described; while the film formed after dissolving into a solvent is used as it is to execute the measurement in case of a polymer.

TABLE 1

| | Number of Compound | Ionization Potential (eV) | Mobility ($cm^2$/Vs)@30 V |
|---|---|---|---|
| Example 1 | 2 | 5.62 | 2.31E−06 |
| Example 2 | 6 | 5.63 | 3.10E−06 |
| Example 3 | 11 | 5.60 | 1.27E−06 |
| Example 4 | (1) | 5.76 | 7.30E−05 |
| Comparative Example 1 | MEH-PPV | 5.00 | 5.00E−05 |

From the results shown in Table 1, it is found that all the quinoxaline-containing compounds and the quinoxaline-containing compound polymers according to the exemplary embodiment have high mobility and charge transporting property, respectively.

What is claimed is:

1. A quinoxaline-containing compound represented by the following formula (I):

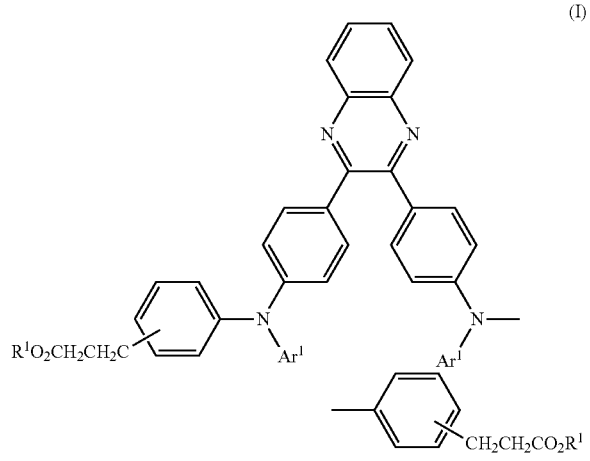

wherein $Ar^1$ represents a substituted or unsubstituted monovalent aromatic group; and $R^1$ represents a hydrogen atom, a substituted or unsubstituted alkyl group, a substituted or unsubstituted aryl group, or a substituted or unsubstituted aralkyl group.

2. The quinoxaline-containing compound according to claim 1, wherein, in the formula (I), the substituents —$CH_2CH_2CO_2R^1$ bind to respective 3'-positions of the phenyl group.

3. The quinoxaline-containing compound according to claim 1, wherein, in the formula (I), the substituents —$CH_2CH_2CO_2R^1$ bind to respective 4'-positions of the phenyl group.

4. The quinoxaline-containing compound according to claim 2, wherein, in the formula (I), $Ar^1$ represents a phenyl group and $R^1$ represents a hydrogen atom.

5. The quinoxaline-containing compound according to claim 3, wherein, in the formula (I), $R^1$ represents a methyl group and $Ar^1$ is selected from the following groups

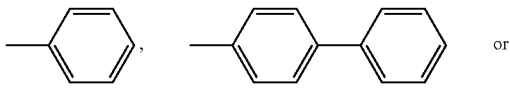 or

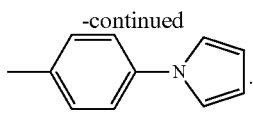

6. The quinoxaline-containing compound according to claim 3, wherein, in the formula (I), $R^1$ represents —$CH_2CH_2CH_2CH_2CH_2CH_3$ and $Ar^1$ represents the following group.

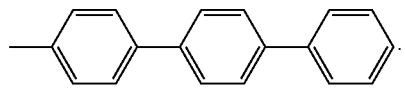

7. A quinoxaline-containing compound polymer represented by the following formula (II):

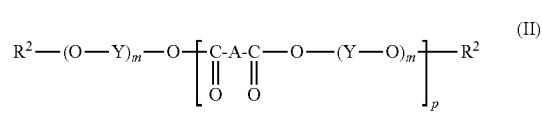

wherein Y represents a substituted or unsubstituted divalent hydrocarbon group; $R^2$ represents a hydrogen atom, a substituted or unsubstituted alkyl group, a substituted or unsubstituted aryl group, or a substituted or unsubstituted aralkyl group; m is an integer of from 1 to 5; p is an integer of from 5 to 5,000; and A is a group represented by the following structural formula (III):

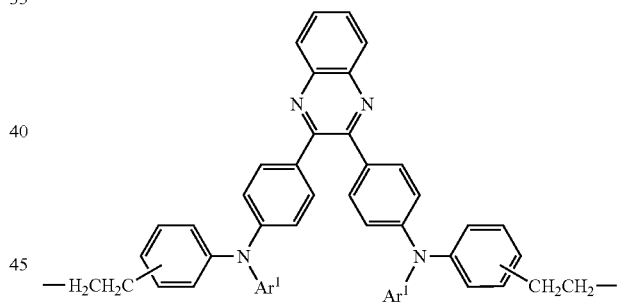

wherein $Ar^1$ represents a substituted or unsubstituted monovalent aromatic group.

* * * * *